United States Patent
Chang et al.

(10) Patent No.: US 10,463,909 B2
(45) Date of Patent: Nov. 5, 2019

(54) SYSTEM AND METHOD FOR USING PERFORMANCE SIGNATURES

(71) Applicant: SEISMIC HOLDINGS, INC., Menlo Park, CA (US)

(72) Inventors: Andrew Robert Chang, Sunnyvale, CA (US); Chung-Che Charles Wang, Palo Alto, CA (US)

(73) Assignee: SEISMIC HOLDINGS, INC., Menlo Park, CA (US)

( * ) Notice: Subject to any disclaimer, the term of this patent is extended or adjusted under 35 U.S.C. 154(b) by 64 days.

(21) Appl. No.: 15/388,670

(22) Filed: Dec. 22, 2016

(65) Prior Publication Data

US 2017/0182360 A1    Jun. 29, 2017

Related U.S. Application Data

(60) Provisional application No. 62/271,313, filed on Dec. 27, 2015.

(51) Int. Cl.
*A63B 22/06* (2006.01)
*G06F 7/02* (2006.01)
(Continued)

(52) U.S. Cl.
CPC ........ *A63B 22/0605* (2013.01); *A61B 5/1118* (2013.01); *A63B 21/06* (2013.01);
(Continued)

(58) Field of Classification Search
CPC ............ A63B 24/0003; A63B 2220/62; A63B 2220/20; A63B 22/0605; G06F 7/02; H04L 63/0861
See application file for complete search history.

(56) References Cited

U.S. PATENT DOCUMENTS

| 4,633,094 A | 12/1986 | Knudsen |
| 5,143,088 A | 9/1992 | Marras et al. |

(Continued)

FOREIGN PATENT DOCUMENTS

| WO | 2011064705 A1 | 6/2011 |
| WO | 2011133799 A1 | 10/2011 |

(Continued)

OTHER PUBLICATIONS

Clifford, Michelle and Gomez, Leticia (2005), "Measuring Tilt with Low-g Accelerometers", in Freescale Semiconductor Application Note, (accessible at http://www.freescale.com/files/sensors/doc/app_note/AN3107.pdf), pp. 01-8.

(Continued)

*Primary Examiner* — Xuan M Thai
*Assistant Examiner* — Malinda D. Blaise
(74) *Attorney, Agent, or Firm* — Van Court & Aldridge LLP

(57) ABSTRACT

A system and method for using performance signatures can include generating a set of performance features during an activity of the first participant by collecting kinematic data from at least one inertial measurement unit and generating a set of biomechanical signals; combining the set of performance features into the performance signature; generating at least a second performance signature from a set of participants; comparing the performance signature of the first participant to at least the second performance signature; and applying a result of the comparison to an interaction with at least one participant.

20 Claims, 19 Drawing Sheets

(51) Int. Cl.

| | | |
|---|---|---|
| *H04L 29/06* | (2006.01) | |
| *G06F 21/32* | (2013.01) | |
| *A63B 21/06* | (2006.01) | |
| *A63B 22/02* | (2006.01) | |
| *A61B 5/11* | (2006.01) | |
| *G06K 9/00* | (2006.01) | |
| *A63B 71/06* | (2006.01) | |
| *A63B 69/00* | (2006.01) | |
| *A63B 69/16* | (2006.01) | |
| *A63B 69/36* | (2006.01) | |
| *A63B 69/18* | (2006.01) | |
| *A63B 69/06* | (2006.01) | |
| *A63B 69/38* | (2006.01) | |
| *A63B 22/04* | (2006.01) | |
| *A63B 24/00* | (2006.01) | |

(52) U.S. Cl.
CPC .............. *A63B 22/025* (2015.10); *G06F 7/02* (2013.01); *G06F 21/32* (2013.01); *G06K 9/00342* (2013.01); *H04L 63/0861* (2013.01); *A61B 2503/10* (2013.01); *A63B 22/0242* (2013.01); *A63B 22/04* (2013.01); *A63B 22/0664* (2013.01); *A63B 24/0087* (2013.01); *A63B 69/00* (2013.01); *A63B 69/002* (2013.01); *A63B 69/0002* (2013.01); *A63B 69/0022* (2013.01); *A63B 69/0024* (2013.01); *A63B 69/0028* (2013.01); *A63B 69/0071* (2013.01); *A63B 69/06* (2013.01); *A63B 69/16* (2013.01); *A63B 69/18* (2013.01); *A63B 69/3608* (2013.01); *A63B 69/38* (2013.01); *A63B 71/0622* (2013.01); *A63B 2024/0009* (2013.01); *A63B 2024/0015* (2013.01); *A63B 2024/0093* (2013.01); *A63B 2069/0008* (2013.01); *A63B 2071/0625* (2013.01); *A63B 2071/0655* (2013.01); *A63B 2220/10* (2013.01); *A63B 2220/12* (2013.01); *A63B 2220/17* (2013.01); *A63B 2220/18* (2013.01); *A63B 2220/20* (2013.01); *A63B 2220/30* (2013.01); *A63B 2220/34* (2013.01); *A63B 2220/40* (2013.01); *A63B 2220/53* (2013.01); *A63B 2220/70* (2013.01); *A63B 2220/73* (2013.01); *A63B 2220/75* (2013.01); *A63B 2220/76* (2013.01); *A63B 2220/78* (2013.01); *A63B 2220/803* (2013.01); *A63B 2220/806* (2013.01); *A63B 2220/807* (2013.01); *A63B 2220/833* (2013.01); *A63B 2220/836* (2013.01); *A63B 2225/50* (2013.01); *A63B 2244/09* (2013.01)

(56) References Cited

U.S. PATENT DOCUMENTS

| | | | |
|---|---|---|---|
| 5,158,089 A | 10/1992 | Swezey et al. | |
| 5,388,591 A | 2/1995 | Luca et al. | |
| 5,398,697 A | 3/1995 | Spielman | |
| 5,749,838 A | 5/1998 | Kline | |
| 5,916,181 A | 6/1999 | Socci et al. | |
| 5,919,149 A | 7/1999 | Allum | |
| 6,032,530 A | 3/2000 | Hock | |
| 6,571,193 B1 * | 5/2003 | Unuma | A43B 3/0005 340/853.2 |
| 7,264,554 B2 | 9/2007 | Bentley | |
| 7,431,703 B2 | 10/2008 | Salvi et al. | |
| 7,602,301 B1 | 10/2009 | Stirling et al. | |
| 7,634,379 B2 | 12/2009 | Noble | |
| 7,698,830 B2 | 4/2010 | Townsend et al. | |
| 8,206,325 B1 | 6/2012 | Najafi et al. | |
| 8,408,041 B2 | 4/2013 | Ten Kate et al. | |
| 8,749,391 B2 | 6/2014 | Flinsenberg et al. | |
| 8,773,256 B2 | 7/2014 | Ten et al. | |
| 8,924,248 B2 | 12/2014 | Tropper et al. | |
| 8,928,484 B2 | 1/2015 | Chang et al. | |
| 9,011,352 B2 | 4/2015 | Ten Kate et al. | |
| 9,128,521 B2 | 9/2015 | Chang et al. | |
| 9,286,782 B2 | 3/2016 | Chang et al. | |
| 2003/0050546 A1 | 3/2003 | Desai et al. | |
| 2003/0181832 A1 | 9/2003 | Carnahan et al. | |
| 2004/0015103 A1 | 1/2004 | Aminian et al. | |
| 2005/0126026 A1 | 6/2005 | Townsend et al. | |
| 2006/0025229 A1 * | 2/2006 | Mahajan | A63B 24/0003 473/131 |
| 2006/0136173 A1 * | 6/2006 | Case, Jr. | A63B 24/00 702/182 |
| 2007/0015611 A1 | 1/2007 | Noble et al. | |
| 2007/0062279 A1 | 3/2007 | Chan et al. | |
| 2007/0115277 A1 | 5/2007 | Wang et al. | |
| 2007/0118056 A1 | 5/2007 | Wang et al. | |
| 2007/0167671 A1 | 7/2007 | Miller | |
| 2008/0204225 A1 * | 8/2008 | Kitchen | A63B 21/072 340/539.22 |
| 2008/0288026 A1 | 11/2008 | Cross et al. | |
| 2008/0319352 A1 | 12/2008 | Chow et al. | |
| 2009/0069722 A1 | 3/2009 | Flaction et al. | |
| 2009/0076419 A1 | 3/2009 | Namineni et al. | |
| 2009/0312973 A1 | 12/2009 | Hatlestad et al. | |
| 2010/0152622 A1 | 6/2010 | Teulings | |
| 2010/0205541 A1 | 8/2010 | Rapaport et al. | |
| 2010/0211349 A1 | 8/2010 | Flaction et al. | |
| 2010/0298655 A1 | 11/2010 | McCombie et al. | |
| 2010/0312152 A1 | 12/2010 | Sarkodie-Gyan et al. | |
| 2010/0317489 A1 | 12/2010 | Flaction | |
| 2011/0063114 A1 | 3/2011 | Ikoyan | |
| 2011/0172951 A1 | 7/2011 | Schlumbohm | |
| 2011/0207581 A1 | 8/2011 | Flaction | |
| 2011/0264325 A1 | 10/2011 | McLaughlin et al. | |
| 2012/0016624 A1 | 1/2012 | Caritu et al. | |
| 2012/0050529 A1 * | 3/2012 | Bentley | G01S 19/19 348/139 |
| 2012/0053890 A1 | 3/2012 | Acht et al. | |
| 2013/0015976 A1 | 1/2013 | Chang et al. | |
| 2013/0053190 A1 * | 2/2013 | Mettler | G09B 19/0038 473/463 |
| 2013/0084805 A1 | 4/2013 | Pasquero et al. | |
| 2013/0128022 A1 * | 5/2013 | Bose | H04N 7/18 348/77 |
| 2013/0158365 A1 | 6/2013 | Chey et al. | |
| 2013/0190657 A1 | 7/2013 | Flaction et al. | |
| 2013/0190658 A1 | 7/2013 | Flaction et al. | |
| 2013/0207889 A1 | 8/2013 | Chang et al. | |
| 2014/0228985 A1 | 8/2014 | Elliott et al. | |
| 2014/0244009 A1 | 8/2014 | Mestas et al. | |
| 2014/0270387 A1 | 9/2014 | Hoof et al. | |
| 2014/0277633 A1 | 9/2014 | Flaction | |
| 2014/0364769 A1 | 12/2014 | Chang et al. | |
| 2015/0040669 A1 | 2/2015 | Borkholder et al. | |
| 2015/0100141 A1 | 4/2015 | Hughes | |
| 2015/0228118 A1 | 8/2015 | Eade et al. | |
| 2016/0014826 A1 | 1/2016 | Mizikovsky et al. | |
| 2016/0042529 A1 | 2/2016 | Tao et al. | |
| 2016/0051858 A1 | 2/2016 | Flaction et al. | |
| 2016/0058367 A1 * | 3/2016 | Raghuram | A61B 5/486 600/479 |
| 2016/0128619 A1 | 5/2016 | Geller et al. | |
| 2017/0095181 A1 | 4/2017 | Hauenstein et al. | |
| 2017/0095692 A1 | 4/2017 | Chang et al. | |
| 2017/0095693 A1 | 4/2017 | Chang et al. | |
| 2017/0182360 A1 | 6/2017 | Chang et al. | |
| 2017/0188894 A1 | 7/2017 | Chang et al. | |
| 2017/0232324 A1 * | 8/2017 | Mettler May | G06K 9/00335 473/459 |
| 2017/0258374 A1 | 9/2017 | Ly et al. | |

(56) References Cited

U.S. PATENT DOCUMENTS

2017/0273601 A1    9/2017    Wang et al.
2017/0344919 A1    11/2017    Chang et al.

FOREIGN PATENT DOCUMENTS

WO    2013024461 A1    2/2013
WO    2015069124 A1    5/2015

OTHER PUBLICATIONS

Kesson, Malcolm (2002), "Mel. Align Y Axis to Vector", in CG References & Tutorials at Fundza.com (accessible at http://www.fundza.com/mel/axis_to_vector/align_axis_to_vector.html), pp. 1-6.

Patel, A.T. and Ogle, Abna A. (2000), "Diagnosis and Management of Acute Low Back Pain", in American Family Physician 15:61 (6) (accessible at http://aafp.org/afp/2000/0315/p1779.html), pp. 1779-1786.

Unknown (2000), "Information from Your Family Doctor Acule Low Back Pain", in American Family Physic1an 15 51 (6) (accessible at http://www.aafp.org/afp/2000/0315/p1789 html), pp. 1-4.

Unknown, "Accelerometer", in Wikipedia (archived Apr. 1, 2011 at http:i/web archive.org/V\leb/2011 0401205940/http://en.wikipedia.org/wiki/Accelerometer), pp. 1-21.

Unknown, "Back Pain", in Wikipedia (archived Feb. 25, 2011 at http:I/web.archive.org/web/20110225132'125/ 0http://en.wikipedia.orgiwiki/Back~pain)... pp. 1-22.

Unknown, "Mahalanobis Distance", in Wikipedia (ard1ived Mar. 29, 2010 at http://web.archive.orf!/ 0 webi20100329232341/http://len.wikipedia.org.l'<>viki/Mahalanobis_distance), pp. 1-8.

Unknown, "Rotation", in Wikipedia (archived I'vlarch 31, 2011 at http://web archive.org/web/20110331232736/http://en.wikipedia.org/wiki/Rotation), pp. 1-13.

Unknown, "A Patient's Guide to Rehabilitation for Low Back Pain", University of Maryland Spine Program (archived 8 Jun. 7, 2011 at http://web.archive.org/web/20110607181952/http://www.umm.edu/spinecenter/education/rehabilitation_for_low_back_pain.htm). pp. 1-10.

Unknown, "Sensors", at freescale.com (accessed May 14, 2012 at http://www.freescale.com/webapp/sps/site/homepage.jsp?nodel=011269). pp. 1-2.

Unknown, "Neutral Spine", in Wikipedia (archived Feb. 12, 2011 at http://web.archive.org/web/20110212145135/http://en.wikipedia.orglwiki/Neutral_spine), pp. 1-7.

\* cited by examiner

SYSTEM AND METHOD FOR USING PERFORMANCE SIGNATURES

CROSS-REFERENCE TO RELATED APPLICATIONS

This Application claims the benefit of U.S. Provisional Application No. 62/271,313, filed on 27 Dec. 2015, which is incorporated in its entireties by this reference.

TECHNICAL FIELD

This invention relates generally to the field of activity tracking, and more specifically to a new and useful system and method for using performance signatures.

BACKGROUND

Within sports, there are numerous styles of performing some action, whether it's how to swing a golf club, shooting a basketball or how to best run a race for example. There is usually no universally preferred style, and even if there were one, people's individual style would vary greatly person to person. How a person performs an action can be influenced by body build, level of fitness, experience, previous coaching, and even cultural impacts. Furthermore, even if an individual has a style to which they aspire, an individual has limited resources to ascertain how their own way of performing an action compares. Professional athletes may have coaches and trainers that can provide detailed guidance. In some cases, the athletes have access to laboratories where their form can be analyzed in a controlled environment. However, most people and even many professionals do not have access to such resources all the time. Such problems of performance styles and lack of access to guidance are evident in other sports and activities as well. Thus, there is a need in the activity monitoring field to create a new and useful system and method for using performance signatures. This invention provides such a new and useful system and method.

DESCRIPTION OF THE EMBODIMENTS

Figure 1:
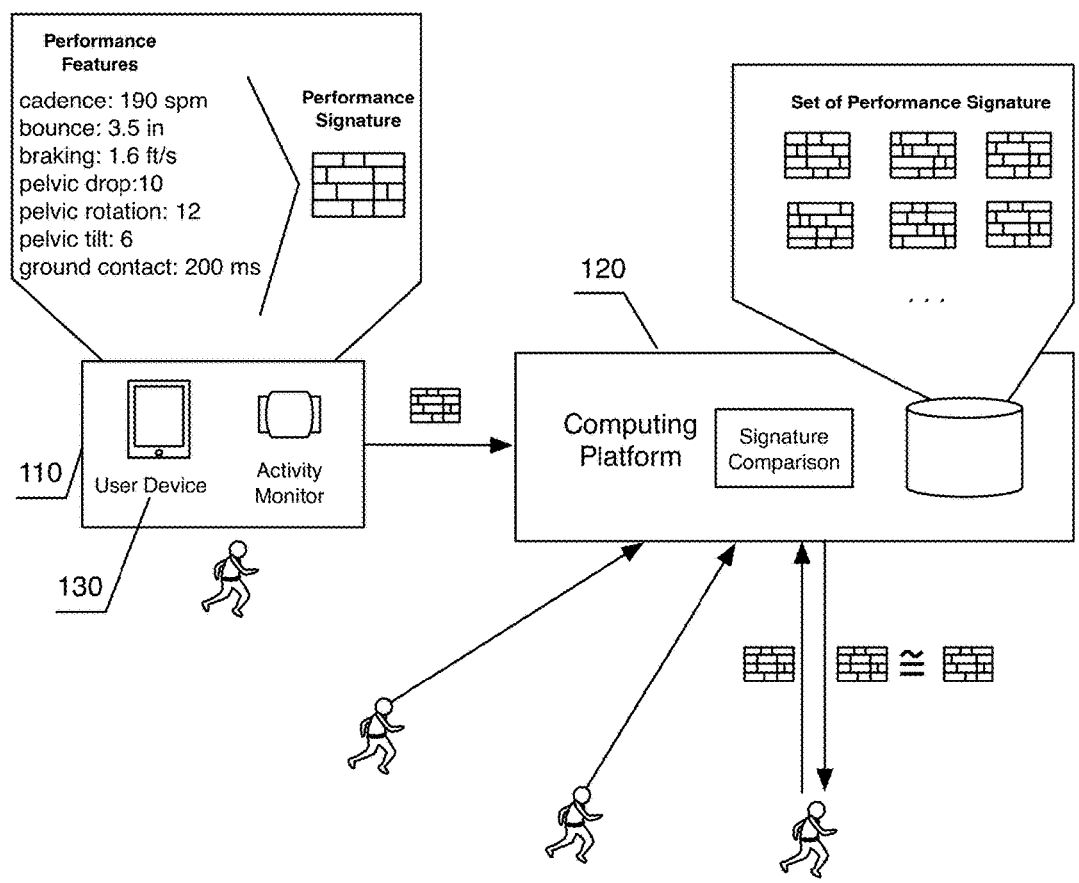
FIG. 1 is a schematic representation of a system of a preferred embodiment.

The following description of the embodiments of the invention is not intended to limit the invention to these embodiments but rather to enable a person skilled in the art to make and use this invention.

1. Overview

A system and method for using an activity performance signature functions to classify or characterize an athlete's performance style and apply that to understanding and altering how the athlete performs an action. The system and method can utilize biomechanical kinematic sensing technology and detected biomechanical signals to establish a performance signature. The system and method preferably utilize an activity monitoring device that is mobile and convenient for monitoring an activity during regular participation. The system and method preferably do not depend on obstructive equipment or highly controlled environments. The system and method can be used for a variety of different activities.

Herein, the system and method are primarily described as it may relate to the exemplary activities of running and golf, but the system and method can be similarly applied to other suitable sports. Individual sports and in particular race-based or skill based sports like track and field sports, biking, swimming, speed skating, skiing, snowboarding, rowing, weight lifting and other such sports can have performance signatures for particular regularly repeated actions. Sports involving a isolated actions such as swinging a golf club, swinging a tennis racket, swinging a baseball bat, throwing a ball, shooting a basketball, kicking a soccer ball, lifting a weight, and the like may additionally benefit from use of the system and method.

The system and method can similarly be applied in the context of team sports such as basketball, football, soccer, baseball, hockey, and the like. Team sports may have various signatures defined according to position, role, or style of play. The signatures for these various sports and activities can each be uniquely customized to the sport. For example shot-put can have a throwing signature; skiing can have a slalom skiing signature; and soccer can have a dribbling signature. There may additionally be a set of different signatures that can be used within a single sport. For example, basketball could have a jump shot signature and a layup signature.

The system and method can additionally be used for non-athletic applications such as medical rehabilitation, ergonomics correction, and other use cases. For example, a general purpose application can implement user identification and/or authentication through a walking signature. In addition, if the user is unknown, the walking signature can be used in identifying similar walking signature classifications, which can be used in classifying the user based on gender, age, ethnicity, geographic, fitness level, health status. For example, a walking performance signature may be used in detecting certain gait disorders through movement.

Herein, the system and method are primarily described as being used with a human participant, but the system and method could alternatively be used with other types of animals such as a dog, a horse, and the like. For example, the running performance signatures of horses could be analyzed and compared when training a racehorse.

In the case of running, there are a variety of running styles for different users. These varying styles of running can be from training, cultural influences, personal physique, and/or other factors. There are different running styles used for casual running, track running, terrain running, half marathons, full marathons, triathlons, ultra marathons, and other suitable running activities. The system and method can facilitate understanding how a particular running signature of a participant relates to reference running signatures.

In the case of golfing, golfers can have different swinging patterns. Swinging patterns may additionally vary between the types of shot or golf club being used. The system and method could facilitate automated golf coaching by analyzing form and guiding them to transition his or her form towards a target performance signature.

In a first use-case, the system and method can be applied to training a user to perform an action in a particular style. This style training can target general performance characteristics, performance characteristics of a group of athletes or for training to be like one individual athlete. For example, an individual could receive automated training to run more like an ultra marathoner. As one potential benefit of the use of performance signatures over a coaching model is that the use of performance signatures can allow for a greater variety of individuality and uniqueness. In one example, the system and method may determine which of a set of potential target performance signatures most closely corresponds to the patterns of a particular participant, and then use that target performance signature as a reference as the participant trains to improve form. This automated process can leverage a spectrum of different performance styles to guide a participant.

In a second use-case, the system and method can be applied to identifying the most similar performance signature. Performance signature matching can be used for matching an individual to a general style but may additionally or alternatively connect an individual with one or more athletes with similar running styles. For example, an individual could see which of their friends have a similar running style, or can find new, relevant training partners. Additionally, different performance styles may benefit from different training routines, which can be provided as a form of recommendations.

In a third use-case, the system and method can be used in combination with an analytics data system. The analytics data system preferably includes data on the results of an action or overall activity. For example performance data for a runner can include average running speed, race time, split times, and other suitable metrics. For golf, the hole map, wind conditions, resulting distance and position, used golf club, and other factors can be collected as input metrics. For basketball, the location on the court of a shot and the result of the attempt (e.g., make or miss) can be supplementary performance data. Other factors such as activity equipment (clothing, bike type, tennis racket type, etc.), the weather, and the like can similarly be collected and used in the analysis. With information on a plurality of users and their performance results, the system and method can detect which performance styles have the best results in different conditions. For example, the method can be used to determine a recommended running style for a half marathoner and another recommended running style for ultra marathoners. In another example, the weather and the race times may be used to generate a running style rating. In another example, the method can be used to determine a recommended golf swing style for driving the ball off the tee and a second recommended golf swing for chipping a ball onto the green. In some cases the performance signature can be applied to keep an individual acting within safe parameters. For example, a weight lifting application can use a generated performance signature to warn a user of improper form and/or to recommend when to increase or decrease weight.

In another use-case, the system and method can be used in user identification, which can be used by a computing device in customizing some experience for that particular user. For example, a treadmill may automatically identify a user based on the observed running signature of the user and adjust training parameters. This can promote a more intuitive user experience where a user can immediately start using a treadmill. In one example, the treadmill speed, resistance, incline, condition duration/patterns, and other variables may be dynamically adjusted according to detected running signatures. Such dynamic equipment adjustments could similarly be applied to elliptical machines, stair climbers, exercise bikes, and/or other pieces of exercise equipment.

2. System

As shown in FIG. 1, a system for using a running signature can include an activity monitor device 110, a computing platform 120, and optionally a secondary computing device 130 in communication with the activity monitor device 110. The system functions to monitor a participant during an activity, produce a performance signature of at least one action performed during the activity, and utilize a comparison of that performance signature and other performance signatures. The system may be customized for one or more types of activities. The various embodiments of the system are preferably configured to facilitate the operation of the method described herein.

Figure 2:
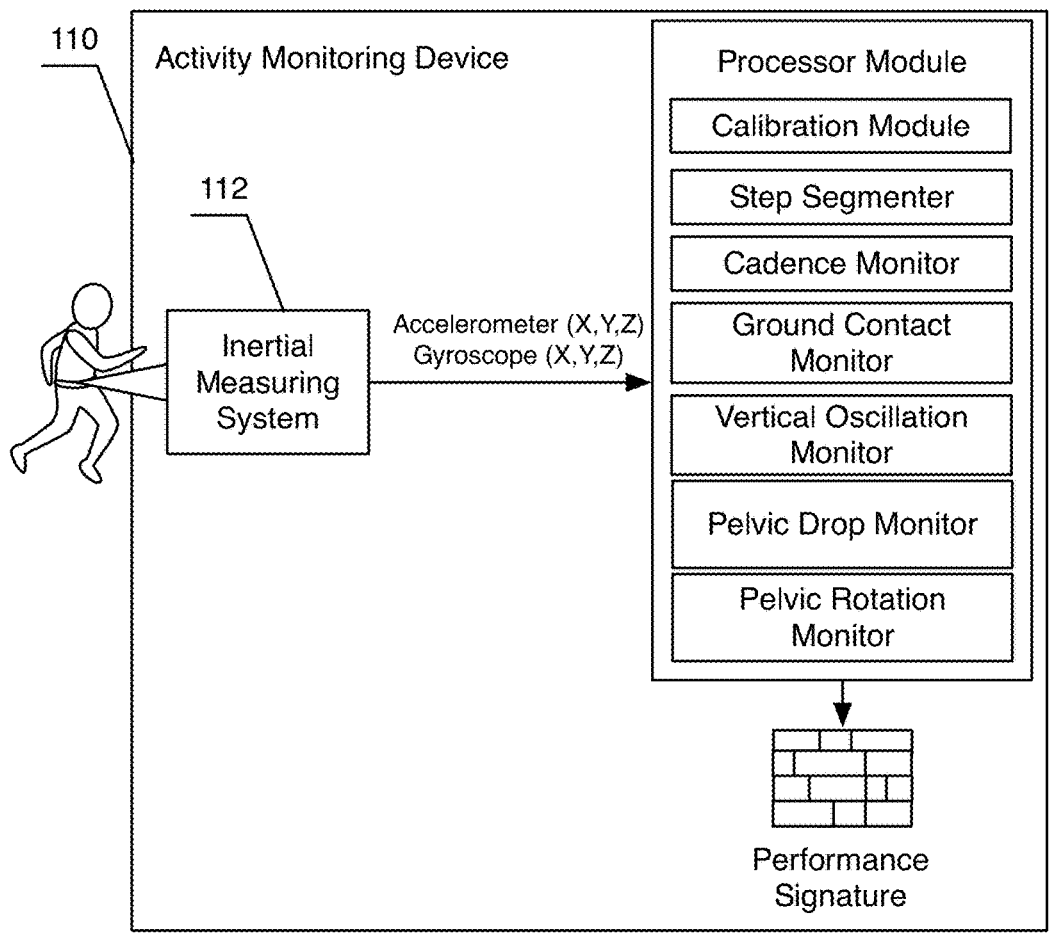
FIG. 2 is a detailed representation of an activity monitoring device generating a performance signature.

A performance signature is preferably a data model characterization of how a participant performs an action. The action is generally part of some activity. Herein, activity is used to classify the context of an action. An activity will preferably have at least one action that is monitored. A sport or exercise classification can be a type of activity. Herein, an action is used to refer to the sequence of kinematic events associated with an event. A stepping motion, object swinging motion, a kicking motion, a throwing motion, a lifting motion, and other motions are examples, of potential motions. A performance signature can be associated with a single particular action (e.g., the most recent golf swing) but may alternatively be associated with a number of actions (e.g., a golf swing signature for all golf swings in the last 3 months). A performance signature is preferably composed of multiple performance features. At least a subset of the performance features are based on biomechanical signals, and the biomechanical signals are preferably based on kinematic data collected from an activity monitor device 110 as shown in FIG. 2.

The activity monitoring device 110 functions to be a motion sensing device coupled to some point affected by the action of a participant. The activity monitor device 110 preferably includes an inertial measurement system 112 and a housing compartment. The activity monitor device 110 can additionally include any suitable components to support computational operation such as a processor, RAM, an EEPROM, user input elements (e.g., buttons, switches, capacitive sensors, touch screens, and the like), user output elements (e.g., status indicator lights, graphical display, speaker, audio jack, vibrational motor, and the like), a communication module or components (e.g., Bluetooth LE, Zigbee, NFC, Wi-Fi, and the like), and/or other suitable components. The activity monitor device is preferably small enough to be mounted to a participant in an unobtrusive way and may be integrated into a wearable such as a belt, a bracelet, a watch, clothing, shoes, or other articles.

The inertial measurement system 112 of the activity monitoring device 110 functions to measure multiple kinematic properties of an activity. The inertial measurement system 112 preferably includes at least one inertial measurement unit (IMU). An IMU can include at least one accelerometer, gyroscope, an inertial sensor, and may additionally include other supporting sensors such as a magnetometer, GPS, EMG, temperature, altimeter, etc. The IMU preferably includes a set of sensors aligned for detection of kinematic properties along three perpendicular axes. In one variation, the inertial measurement unit is a 9-axis motion-tracking device that includes a 3-axis gyroscope, a 3-axis accelerometer, and optionally a 3-axis magnetometer. The inertial measurement system 112 can additionally include an integrated processor that, among other functionality, provides sensor fusion in hardware, which effectively provides a separation of forces caused by gravity from forces caused by speed changes on the sensor. The integrated processor may additionally provide post processing of kinematic data. Preferably kinematic data can be processed into biomechanical signals used as performance features of a performance signature. The on-device sensor fusion may provide other suitable sensor conveniences or sensor data processing.

In one embodiment, the activity monitor device 110 measures kinematic data at a single location. In an alternative embodiment, the activity monitor device 110 comprises multiple inertial measurement systems 112 coupled, attached, or otherwise positioned at different locations. An inertial measurement system 112 can be coupled to a point on the participant's body. For example, a set of inertial measurement systems 112 can be positioned at the waist region, the shank of one or two legs, one or two feet, the thigh of one or two legs, the upper body, the upper arm, the lower arm, the head, or any suitable position on the body. Alternatively, an inertial measurement system 112 can be coupled to a point on a piece of equipment used during the activity such as a golf club, a bike wheel or pedal, a rowing oar, a basketball, a baseball, a baseball bat, a weight lifting bar, a tennis racket, or any suitable piece of equipment. For example one or more inertial measurement system(s) 112 and their associated components (e.g., power source, housing, and communication modules) can be attached to a handle or head of a golf club.

Figure 3A:
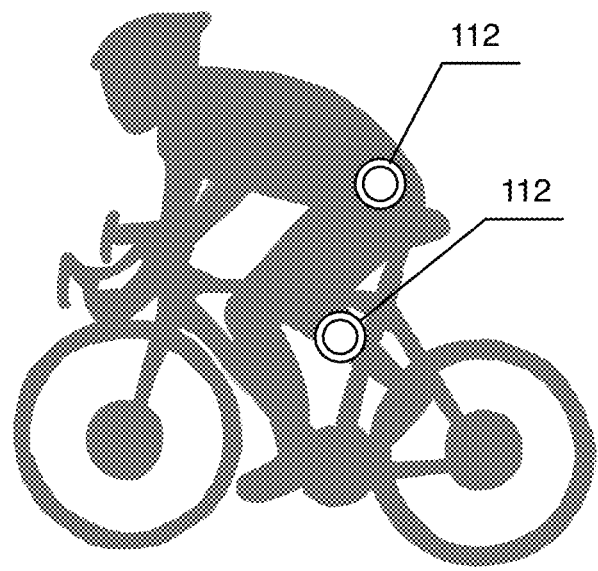
FIGS. 3A-3E are exemplary representations of activity monitoring device positioning for various activities.
Figure 3B:
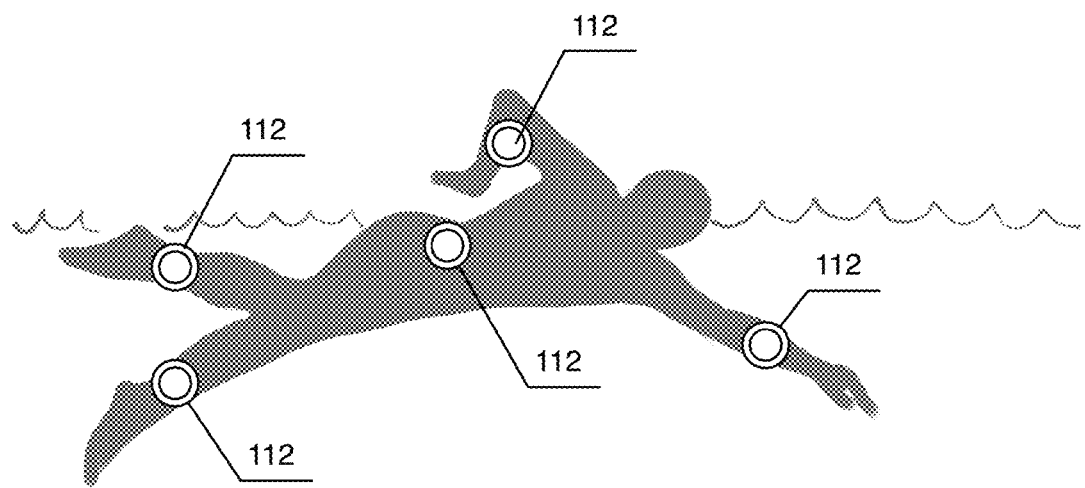
Figure 3C:
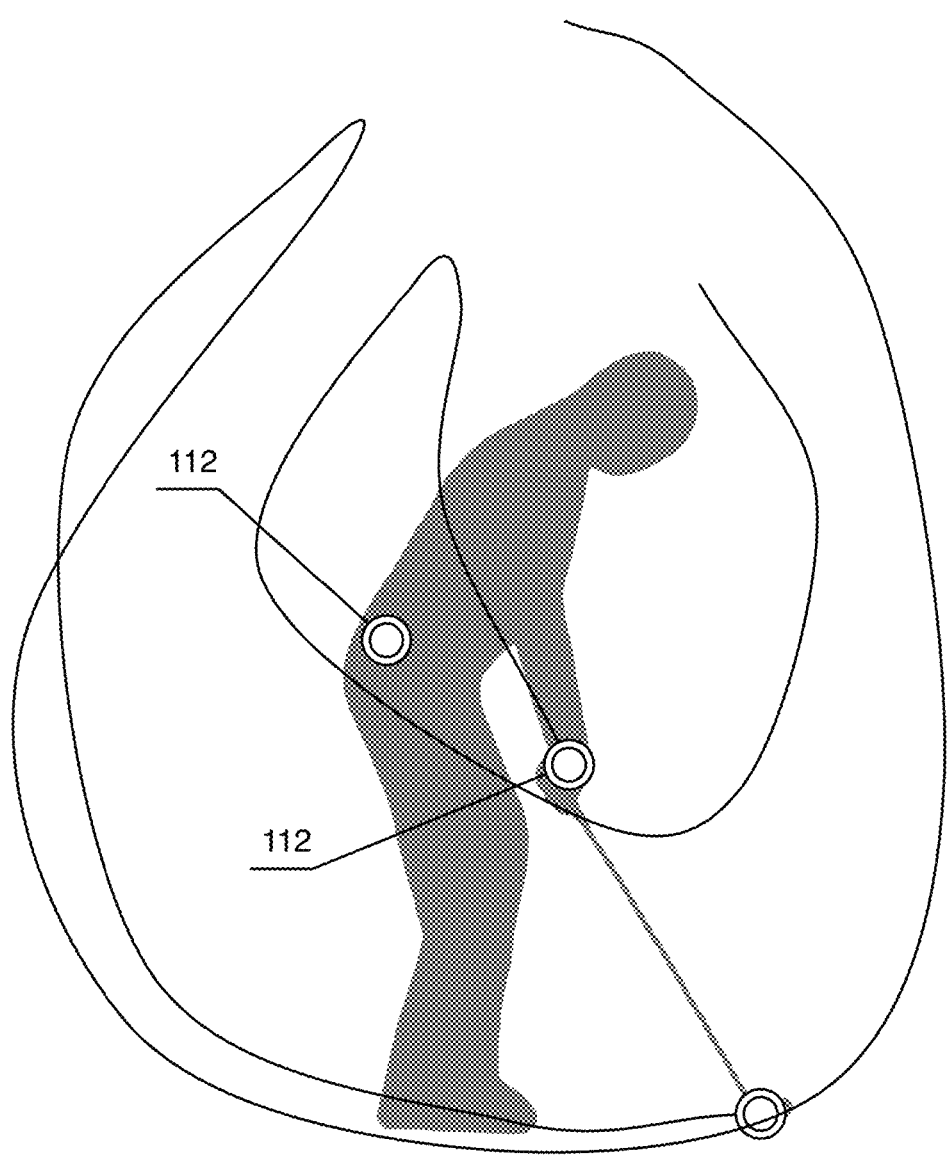
Figure 3D:
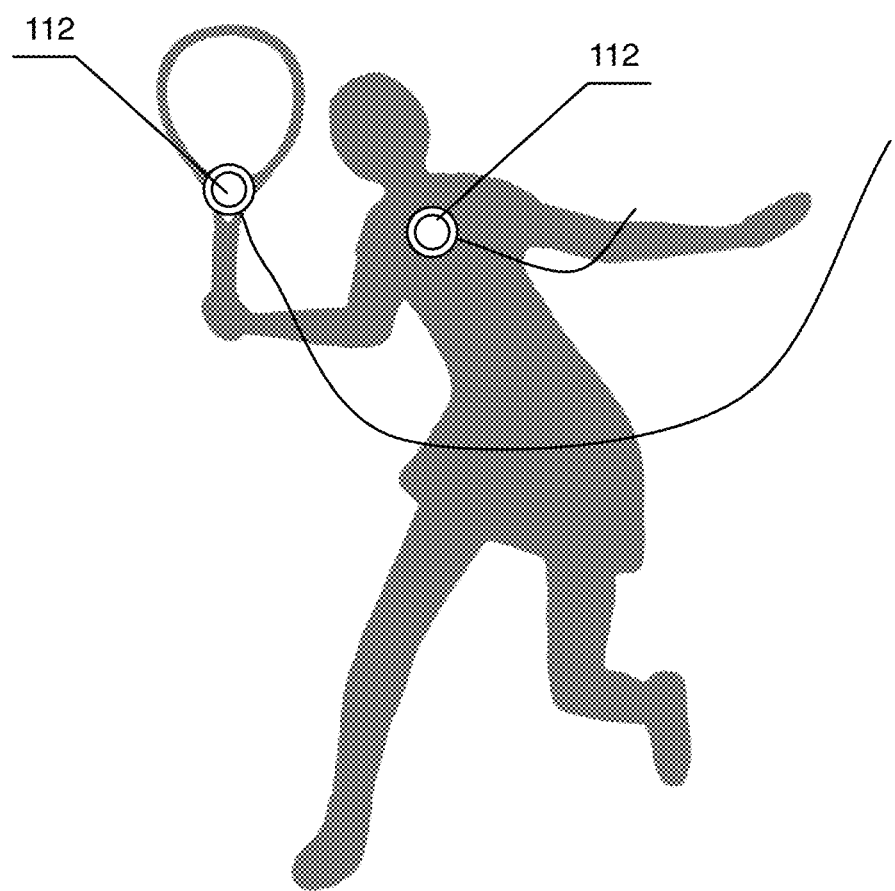
Figure 3E:
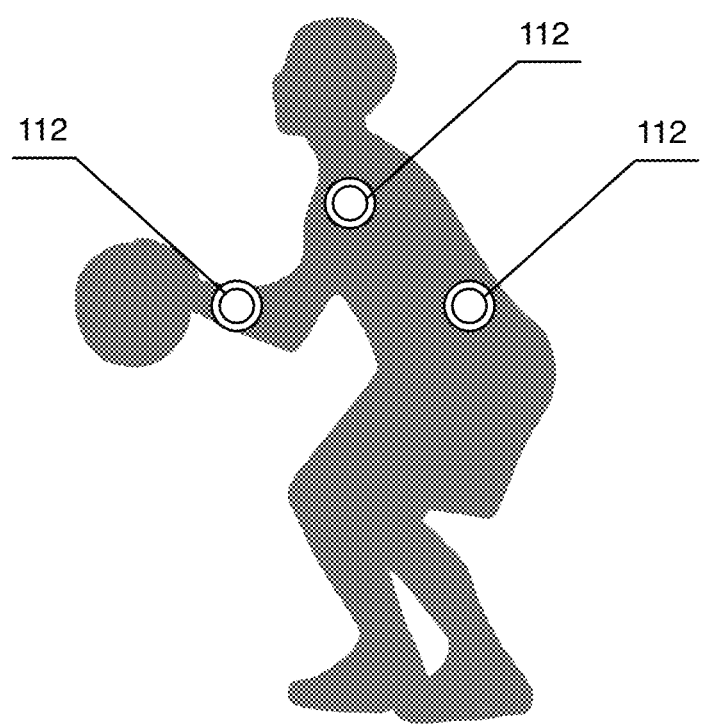

The location or positioning of an activity monitor device no and a set of inertial measurement systems 112 may depend on the activity. As shown in FIG. 3A, a bicyclist may wear an activity monitoring device at the pelvic region and on the leg. As shown in FIG. 3B, a swimmer can wear an inertial measurement system 112 on each limb. As shown in FIG. 3C, a golfer could wear one activity monitoring device 110 to monitor kinematics of the participant's waist and another activity monitoring device 110 to understand the swinging path. A tennis player could similarly use two activity monitoring devices 110 where one is embedded in the racket as shown in FIG. 3D. Multiple activity monitoring devices could additionally be used to characterize the joint angle and motion such as for the shooting motion in basketball as shown in FIG. 3E.

In other variations, the activity monitor device 112 can include an inertial measurement system 112 or other suitable sensing elements within the environment of the activity. For example, a treadmill could include an inertial measurement system 112 integrated into a running platform of the treadmill. The running patterns of a user of the treadmill can be sensed through step impact on the treadmill.

The inertial measurement system(s) 112 can additionally be used in generating biomechanical signals that characterize other aspects of the activity. A biomechanical signal preferably parameterizes a biomechanical-based property of some action by a user. More particularly, a biomechanical signal quantifies at least one aspect of motion that occurs once or repeatedly during an activity. For example, in the case of walking or running, how a participant takes each step can be broken into several biomechanical signals. In a preferred implementation, the system and method for a running use-case preferably operate with a set of biomechanical signals that can include ground contact time, braking, pelvic rotation, pelvic tilt, pelvic drop, vertical oscillation of the pelvis, forward oscillation, forward velocity properties of the pelvis, step duration, stride or step length, step impact or shock, and/or foot pronation. Additionally, the biomechanical signals can include left/right foot detection, which may be applied for further categorizing or segmenting of biomechanical signals according to the current step side. In addition to kinematic measurements, the inertial measurement system(s) 112 can be used in building a motion path reading for one or more points. A motion path can be a one or multi-dimensional representation of motion. For example, the three dimensional motion path of a foot as a function of time can be a step motion path. The activity monitor device can additionally include other sensors such as an altimeter, GPS, magnetometer, or any suitable sensor.

The computing platform 120 functions to collect and process data from a plurality of users. Collection of data from a plurality of participants by the computing platform can enable dynamic and continued refinement of performance signature processing. The computing platform 120 may be used to serve a variety of types of activities. Alternatively, the computing platform 120 may be designed around a single type of activity such as running or golfing. The computing platform 120 can include a user account system. One or more performance signatures can be created for or associated with a user account. Activity data or processed activity data that has been collected from an activity monitor device can be stored in the computing platform. The computing platform is preferably configured to receive various performance signature queries; execute the queries against the collected performance signatures; and generate at least one query response based on a comparison of a performance signature query and at least a second performance signature. The computing platform can include various performance signature processing modules. There can be a performance processing module for comparing performance signatures, a performance processing module for matching performance signatures, a performance processing module for generating training recommendations to transform a first performance signature to a second performance signature, and/or any suitable processing module. The computing platform can support interfacing with various forms of client applications such as native applications, browser applications, specific connected devices, and/or any suitable type of client. In one alternative implementation, the system may be implemented in a non-connected device without the need for a remote computing platform. For example, a set of performance signatures could be preloaded onto a device for local determination of a performance style.

In one preferred implementation, the activity monitor device 110 communicates locally to a secondary computing device 130. The secondary computing device 130 can be a smart phone, a smart watch, a tablet, or any suitable computing device. Data from the activity monitor device 110 can be communicated to the computing platform 120 through the secondary computing device as shown in FIG. 1. The secondary computing device 130 may additionally offer richer user interface elements (e.g., touch input, audio systems, a display, tactile feedback elements, and the like), processing capabilities, application functionality, sensing capabilities. For example, a secondary computing device 130 may collect GPS information and weather information during an activity. In alternative embodiments, the activity monitor device may include communication components to communicate with the computing platform without dependence on a secondary computing device 130.

A user application operable on the secondary computing device 130 or alternatively the activity monitor device 110 can function to provide activity tracking and user feedback in cooperation with the activity monitor device 110. The user application is preferably in communication with the activity monitor device and the computing platform. The user application and the activity monitor device preferably communicate over Bluetooth LE but any suitable communication protocol or medium may be used. The activity monitor device preferably communicates data relating to the kinematic activity to the user application.

A processor of the activity monitor device 110, computing platform 120, and/or the secondary computing device 130 can be configured to facilitate the generation and usage of a performance signature. The process of generating a performance signature may be performed on one device or cooperatively distributed across multiple devices. Preferably, a processor system is configured to isolate kinematic data associated with an action of an activity, generate a set of biomechanical signals, and assemble a set of performance features to generate a performance signature. At least a subset of the performance features is based on the set of biomechanical signals. Isolating kinematic data can include segmenting kinematic data of an activity by consecutively repeated actions. For example, running kinematic data can be segmented by steps, biking kinematic data can be segmented by pedal strokes, and swimming kinematic data can be segmented by swim strokes. Isolating kinematic data may alternatively include detecting or selecting portions of kinematic data associated with an isolated occurrence of one or more actions. For example, selecting and using the kinematic data during a golf swing, a baseball throw, or a tennis swing.

3. Method

Figure 4:
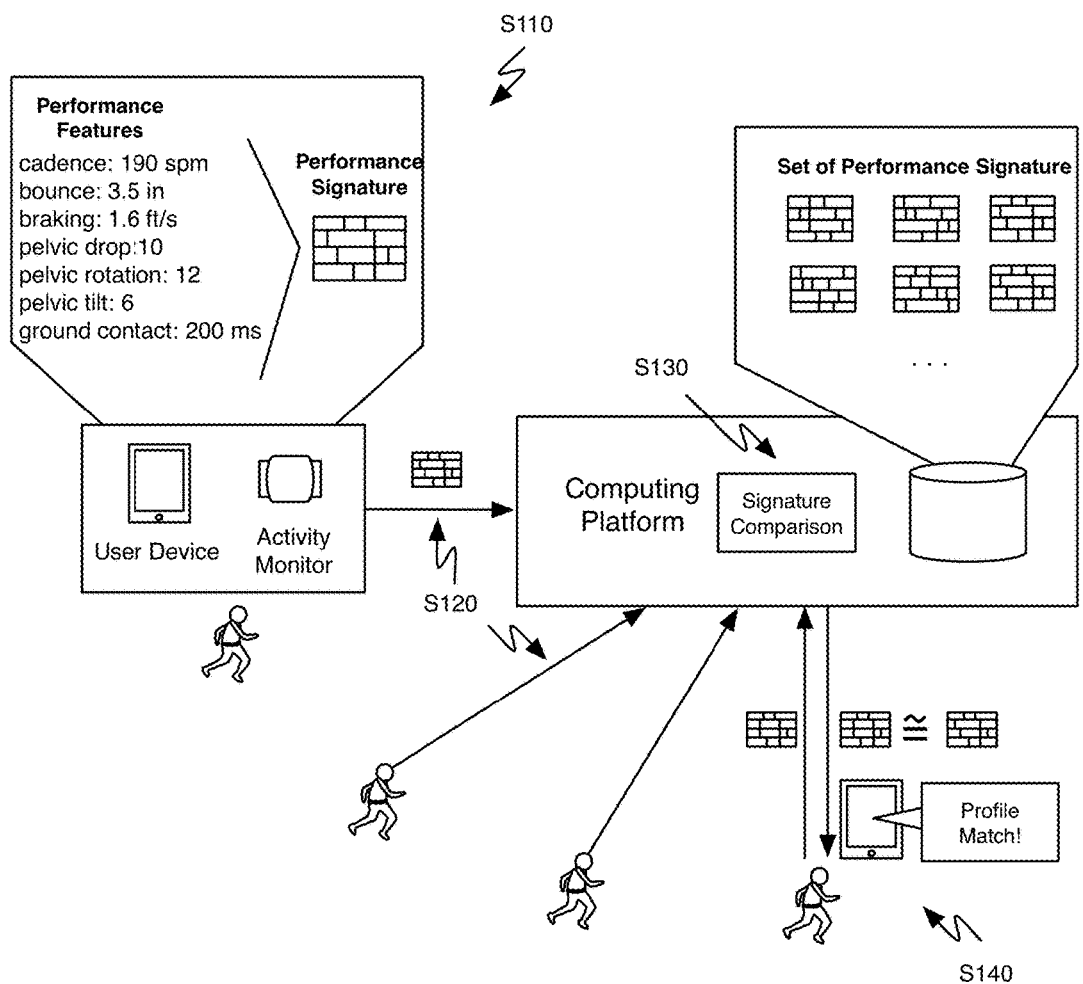
FIG. 4 is a schematic representation of a method of a preferred embodiment.

As shown in FIG. 4, a method for using an activity performance signature of a preferred embodiment can include generating a performance signature of at least one participant performing an activity S110; at a computing platform, collecting performance signatures of a set of participants S120; comparing the performance signature of at least one participant to at least a second performance signature S130; and applying a result of the comparison to an interaction with at least one participant S140. The method primarily functions to characterize the unique motion patterns of a participant during an activity such as running, walking, swimming, biking, exercising, playing a sport, or doing any suitable activity. That performance signature can be used for user identification, classification of users, instructing a user, and other suitable applications.

Figure 5:
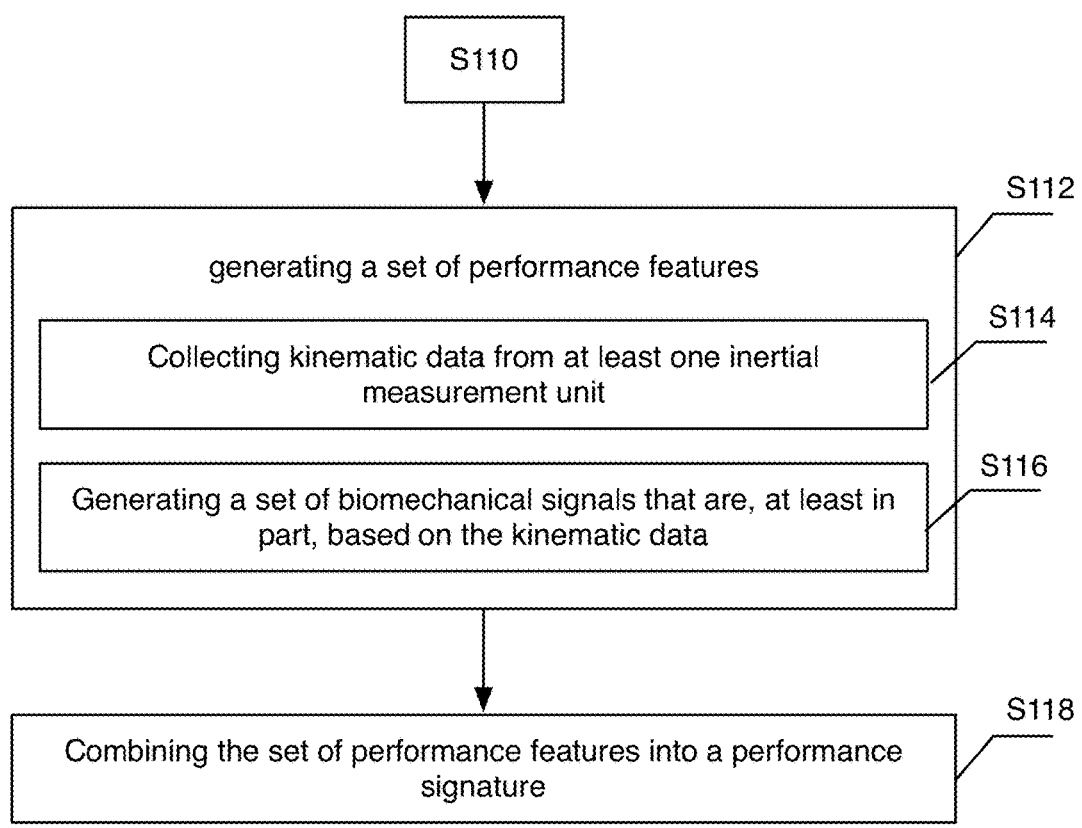
FIG. 5 is a flowchart representation of a variation of generating a performance signature.

Block S110, which includes generating a performance signature of at least one participant performing an activity, functions to establish a characterization of how an individual performs an action. A performance signature can include generating a set of performance features S112 and combining the set of performance features into a performance signature S118. In one preferred implementation, at least a subset of the performance features are generated by collecting kinematic data from at least one inertial measurement unit S114 and generating a set of biomechanical signals that are, at least in part, based on the kinematic data S116 as shown in FIG. 5.

The performance signature is preferably a data model based on kinematic characteristics of how a participant performs an action. A performance signature is preferably generated from observation of multiple samples of an action during an activity. In one class of activity, the action characterized by the performance signature is a repetitive action that is performed one after the other such as steps or arm strokes. Activities with repetitive actions include: running with repetitive steps, swimming with repetitive arm strokes and/or kicks, biking with repetitive pedaling, rowing with repetitive strokes, and/or other suitable activities. In another class of activity, the action characterized by a performance signature is an isolated action that is performed once or a limited amount of times with sustained delays and events between other occurrences of the action. Activities with isolated actions can include: golf with golf swings, weight lifting with individual lifts, soccer with soccer kicks, basketball with shots, baseball with swings and throws, and/or other suitable activities. Additionally, multiple performance signatures may be generated for different actions within one activity.

Block S112, which includes generating a set of performance features functions to assemble various metrics that can be used in characterizing an action. The performance features are preferably measured automatically through one or more sensors attached to the user, sensors attached to equipment or environment, remote sensing elements (such as cameras, 3D scanners, and the like), and/or other suitable elements for the collection of action information. A subset of performance features can relate to measurements of kinematic properties such as linear or rotational displacements, velocities, and accelerations measured at one or more points. The measurements can be associated with particular segments of an action or of a full action. The measurements may be related to extrema, averages, ranges, and the like over the course of an action or segment of an action. The kinematic properties can be measured at points on a participant such as at a pelvic region, a foot, a shin, thigh, upper body, head, upper arm, lower arm, a hand, or other suitable body locations. The kinematic properties can additionally or alternatively be measured at static points on a piece of activity equipment such as on a golf club, a rowing oar, basketball, soccer ball, baseball bat, baseball, tennis racket, weight lifting bar, or other suitable pieces of equipment used during an action.

Preferably, at least a subset of the performance features are generated by collecting kinematic data from at least one inertial measurement unit S114 and generating a set of biomechanical signals that are, at least in part, based on the kinematic data S116. The biomechanical signals parameterize biomechanical movement properties during an action. A biomechanical signal or a set of biomechanical signals can in some cases be used as a performance signature. Blocks S114 and S116 preferably utilize an activity monitoring device worn on a participant. For example, a user could wear an activity monitoring device along the waist region. Alternative implementations may have an activity monitoring device attached or integrated into activity equipment as described above. Similarly, activity monitoring devices and/ or inertial measurement units may be mounted to different points to collect kinematic data at different locations during an action.

In one implementation, the biomechanical signal generation utilizes various approaches to converting kinematic data to biomechanical signals such as those described in the system and method for characterizing biomechanical activity described in U.S. patent application Ser. No. 15/282,998, titled "SYSTEM AND METHOD FOR CHARACTERIZING BIOMECHANICAL ACTIVITY", filed 30 Sep. 2016, which is hereby incorporated in its entirety by this reference.

Block S114, which includes collecting kinematic data from at least one inertial measurement unit, functions to sense, detect, or otherwise obtain motion sensor data. Kinematic data can be collected directly from one or more sensing device(s), but the kinematic data may alternatively be collected from an intermediary data source. A sensing device is preferably an activity monitoring device with at least one inertial measurement unit (e.g., an accelerometer and/or gyroscope), but any suitable sensing system may be used. A sensing device may perform processing operations but a user application or other remote computing resource may additionally or alternatively facilitate processing of kinematic data from a sensor.

The kinematic measurements are preferably along a set of orthonormal axes (e.g., an x, y, z coordinate system). The axis of measurements may not be aligned with a preferred or assumed coordinate system of the activity. Accordingly, the axis of measurement by one or more sensor(s) may be calibrated for analysis. One, two, or all three axes may share some or all features of the calibration, or be calibrated independently. The kinematic measurements can include acceleration, velocity, displacement, force, angular velocity, angular displacement, tilt/angle, and/or any suitable metric corresponding to a kinematic property or dynamic property of an activity. Other forms of kinematic measurements can be these indicators as a function of time, as a function of a metric changing in time, and/or a comparison or relationship of one or more metrics over time. Preferably, a sensing device provides acceleration as detected by an accelerometer and angular velocity as detected by a gyroscope along three orthonormal axes. The set of kinematic data streams preferably includes acceleration in any orthonormal set of axes in three-dimensional space, herein denoted as x, y, z axes, and angular velocity about the x, y, and z axes. Additionally, the sensing device may detect sensor orientation from a magnetic field through a three-axis magnetometer.

Block S116, which includes generating a set of biomechanical signals based on the kinematic data, functions to process and/or parameterize a set of characterizations of motion properties of an activity. The biomechanical signals for an activity are preferably a substantially real-time assessment of the biomechanical properties during the activity, and, as such, the biomechanical signal can be a time series data set. Biomechanical signals could alternatively be generated from pre-recorded kinematic data. Generating a set of biomechanical signals can include normalizing kinematic data or otherwise preparing the kinematic data for processing. Normalizing can involve standardizing the kinematic data and calibrating the kinematic data to a coordinate system of the participant or a piece of equipment. Preprocessing may additionally rectify relative orientations of multiple sensor devices mounted at different points. Single and double integration in combination with error correction can be used with the accelerometer data and gyroscope data along one or more axes. In some cases, right/left detection can be used to differentiate between biomechanics of different sides of the body. The biomechanical signals can reflect ranges in observed metrics and/or maximum, minimum, or average metric values. In some cases multidimensional motion paths can be generated to reflect the state of a kinematic property as a function of time during an action. For example, running path could show the motion path of a participant's hip when running or a golf swing path could show the three-dimensional path of an activity monitoring device during a golf shot.

Part of generating a performance signature can include isolating kinematic data associated with an action of an activity, which may include segmenting the kinematic data and/or identifying and selecting a window of kinematic data associated with an action.

Figure 6:
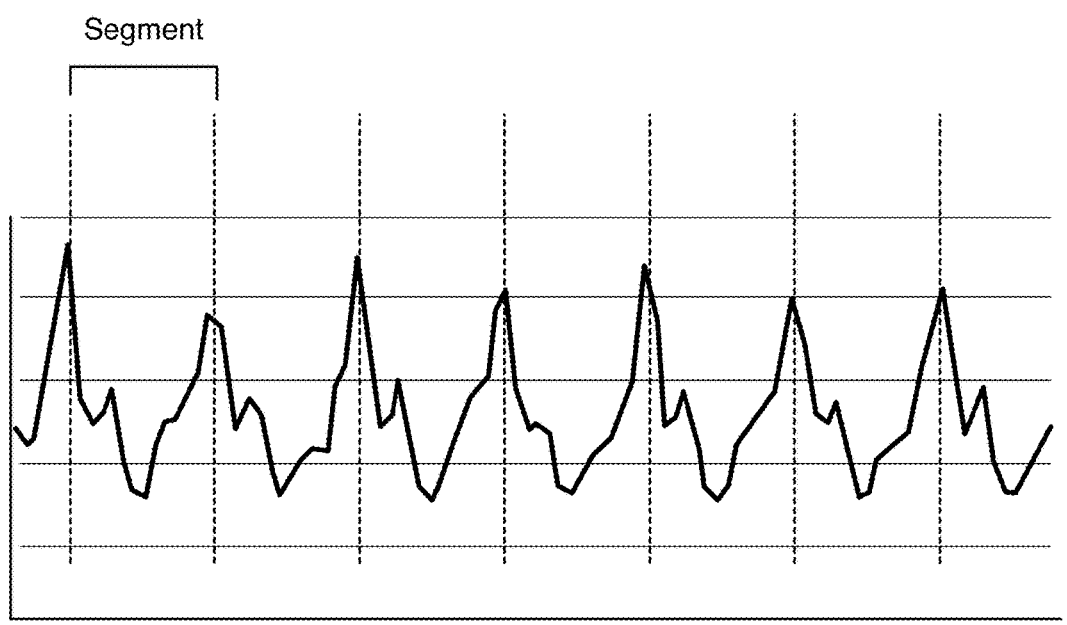
FIG. 6 is a schematic representation of segmenting kinematic data.

In the variations where the activity includes repetitive actions, generating a set of biomechanical signals can include segmenting the kinematic data as shown in FIG. 6. The kinematic data stream are preferably segmented into a consecutive sequence of actions. Biomechanical signals can be generated that reflect the biomechanical or motion properties observed within the action segments. In a running activity, segmenting can be executed for individual steps or for a stride (two consecutive steps). In a swimming activity, segmenting can be executed for individual arm strokes, individual leg kicks, groups of connected actions, or other appropriate action segments that may equate to a swimming stride or other suitable segment. In a biking activity, segmenting can be executed for individual pedal strokes. In the repetitive action variation, the rate of the action may alter the performance signature. Accordingly, the performance signature may be generated for sequences of actions when a second metric is within a specified range. The secondary metric is preferably the pace of the participant, which could be a participant's ground speed, or rate of action repetition. The secondary metric may alternatively be biometric properties such as heart rate or other suitable metrics. In the running use case, a preferred running rate may be determined for a participant. The preferred running rate may be based on the typical running speed of a participant as determined over the running history of the participant. In this way, the running signature of a participant reflects the running patterns of the participant only for portions of the run when running at a typical pace—portions of a run when running up hill, down hill, over rough terrain, or getting tired may not be used for the running signature in this particular example.

Figure 7A:
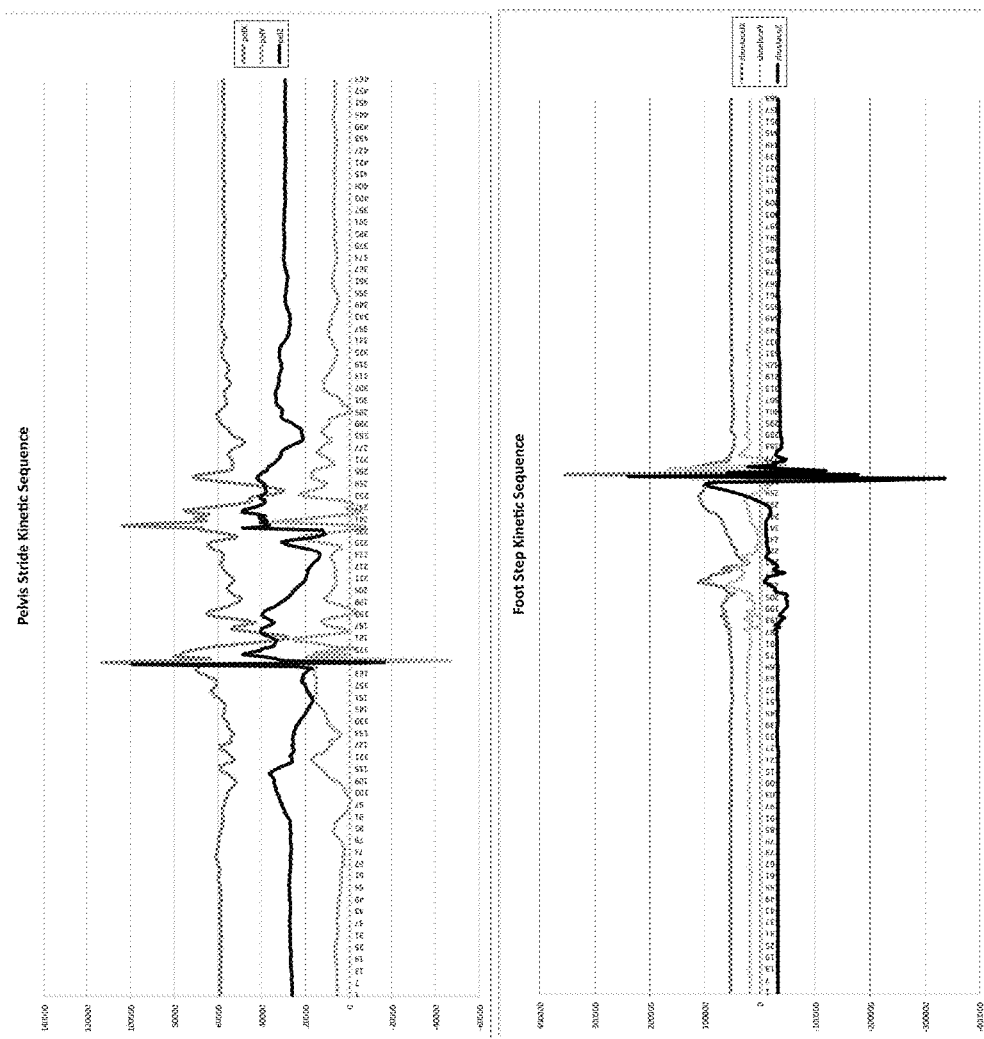
FIG. 7A is a chart representation of an exemplary walking kinetic sequence.
Figure 7B:
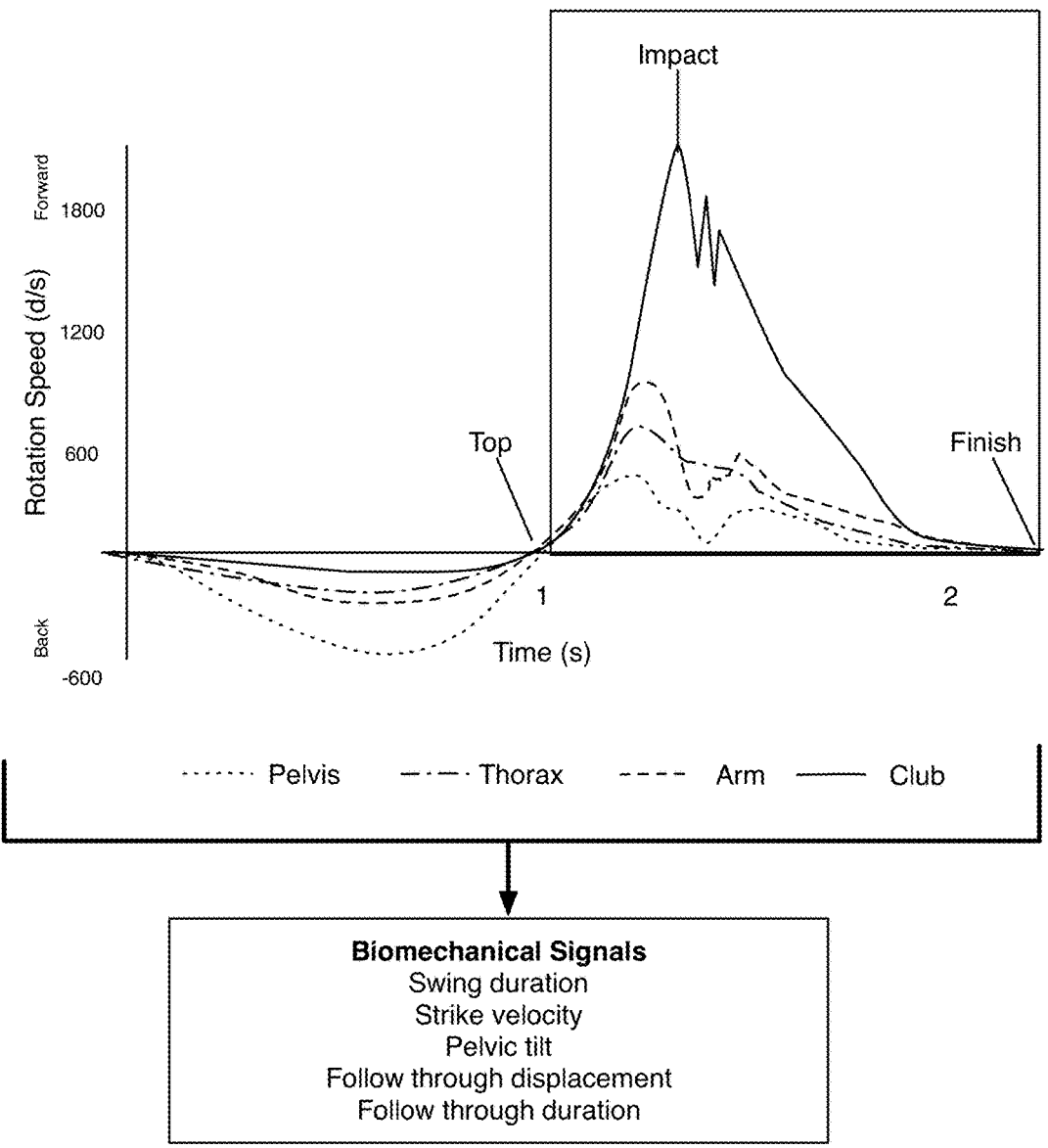
FIG. 7B is a chart representation of an exemplary golfing kinetic sequence and selecting a window of kinematic data.

In the variations where the activity includes isolated actions, generating a set of biomechanical signals can include identifying the action. More specifically, identifying the action comprises identifying and selecting a window of kinematic data associated with an action and generating biomechanical signals from kinematic data within the window as shown in FIG. 7B. In one variation, identifying the action can comprise monitoring the kinematic data, the biomechanical signals, and/or performance features as a function of time and detecting an action pattern. Detecting an action pattern can include the use of heuristical models such as monitoring value threshold conditions, event sequences, and/or other patterns. Detecting an action pattern can additionally or alternatively use machine intelligence such as deep learning, machine learning, statistical methods, and/or other suitable algorithmic approaches to detecting an action. Detection of an action may be made in real-time but may alternatively be retroactive where the action is detected and processed using data before, during, and after the action. For example, biomechanical signals may be actively collected as a participant is playing basketball. Most of the kinematic data may be ignored with regard to creating a jump shot performance signature, but upon attempting a jump shot the patterns in the kinematic data are classified as a jump shot action, and the jump shot action can be used in generating and/or updating a performance signature. In one variation, detecting action pattern may include detecting an initial body position and the transition into an intermediary position of the action. In a golfing example, the ready stance of a golfer before swing could be detected based on the orientation of the activity monitor device and the user.

In golf, baseball, and other sports there may additionally be an impulse event that can be detected, wherein an impulse could correspond to hitting of a golf ball, hitting of a baseball with a bat, or some other event that causes a sudden change in load or forces. The impulse event could be detected through the kinematic data, but the impulse event could additionally or alternatively use audio data or other sensing capabilities of the system. In some cases, detection of an impulse event may be a condition to consider the action. For example, a golfer may take several practice swings but the impulse event (e.g., detected from an impulse signal evident in the kinematic data or in an audio recording) may be required to determine the action as a real swing. Real golf swings and practice swings could be treated differently when generating a performance signature.

In another variation, identifying an action may be through receiving a user-initiated signal. For example, a participant may activate a swing recording mode within an application that is in communication with an activity monitor device.

Different sets of performance features may be used in characterizing different actions and/or activities. Starting state, intermediary states, and/or ending states of an action and their associated kinematic properties, changes between states, and timing of states can be used to create performance features. For example, in a golf swing action, the kinetic sequence of the pelvis, thorax, arm and club mechanics, the timing of maximum rotation velocities (an example is highlighted in FIG. 7B), club angle, and other mechanics may be used.

Block S118, which includes combining the set of performance features into a performance signature, functions to construct a data object representation of the participant's patterns when performing the pattern. A performance signature preferably enables the actions of a participant to be resolved to one or more classifications. Within broad categories, the performance signature can preferably be used to differentiate between sub groups. For example, a performance signature of a runner may enable them to be grouped with other heel strike runners as well as other styles of running more specific than heel strike runners. A performance signature in some cases may be used to uniquely identify or distinguish a participant.

For a runner, a running signature can include a set of performance features such as includes cadence, ground contact time, braking, pelvic rotation, pelvic tilt, pelvic drop, vertical oscillation of the pelvis, forward oscillation, forward velocity properties of the pelvis, step duration, stride or step length, step impact or shock, foot pronation, body loading ratio, foot lift, motion paths, and/or other features. In combination, the performance features of a running signature can provide an overall descriptor of how a runner runs.

Cadence can be characterized as the step rate of the participant.

Ground contact time is a measure of how long a foot is in contact with the ground during a step. The ground contact time can be a time duration, a percent or ratio of ground contact compared to the step duration, a comparison of right and left ground contact time or any suitable characterization.

Braking or the intra-step change in forward velocity is the change in the deceleration in the direction of motion that occurs on ground contact. In one variation, Braking is characterized as the difference between the minimum velocity and maximum velocity within a step, or the difference between the minimum velocity and the average velocity within a step. Braking can alternatively be characterized as the difference between the minimal velocity point and the average difference between the maximum and minimum velocity. A step impact signal may be a characterization of the timing and/or properties relating to the dynamics of a foot contacting the ground.

Pelvic dynamics can be represented in several different biomechanical signals including pelvic rotation, pelvic tilt, and pelvic drop. Pelvic rotation (i.e., yaw) can characterize the rotation in the transverse plane (i.e., rotation about a vertical axis). Pelvic tilt (i.e., pitch) can be characterized as rotation in the sagittal plane (i.e., rotation about a lateral axis). Pelvic drop (i.e., roll) can be characterized as rotation in the coronal plane (i.e., rotation about the forward-backward axis).

Vertical oscillation of the pelvis is characterization of the up and down bounce during a step (e.g., the bounce of a step).

Forward velocity properties of the pelvis or the forward oscillation can be one or more signals characterizing the oscillation of distance over a step or stride, velocity, maximum velocity, minimum velocity, average velocity, or any suitable property of forward kinematic properties of the pelvis.

Step duration could be the amount of time to take one step. Stride duration could similarly be used, wherein a stride includes two consecutive steps.

Foot pronation could be a characterization of the angle of a foot during a stride or at some point of a stride. Similarly foot contact angle can be the amount of rotation in the foot on ground contact. Foot impact is the upward deceleration that is experienced occurring during ground contact. The body-loading ratio can be used in classifying heel strikers, midfoot, and forefoot strikers. The foot lift can be the vertical displacement of each foot. The motion path can be a position over time map for at least one point of the runner's body. The position is preferably measured relative to the athlete. The position can be measured in one, two, or three dimensions. As a feature, the motion path can be characterized by different parameters such as consistency, range of motion in various directions, and other suitable properties. In another variation, a motion path can be compared based on its shape.

The foot lift can be the vertical displacement of each foot.

Figure 11A:
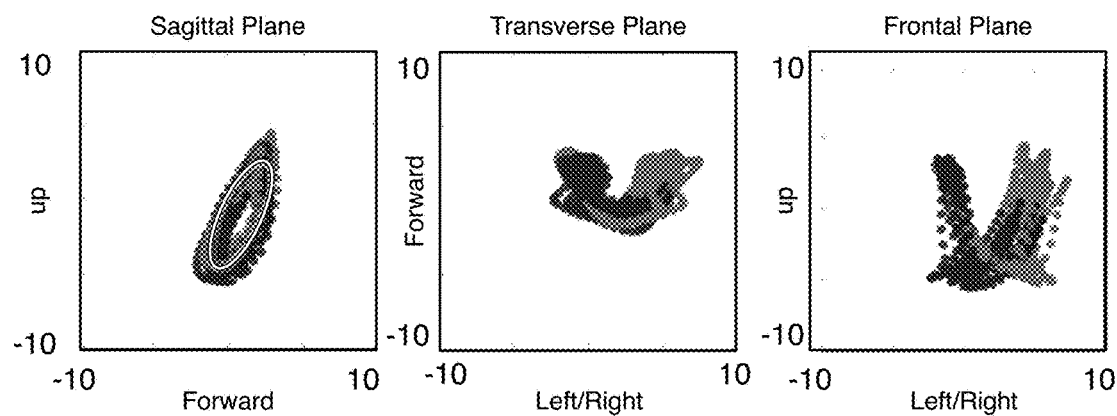
FIGS. 11A-11C are exemplary motion paths of different runners with color to indicate the motion paths of during left and right steps.
Figure 11B:
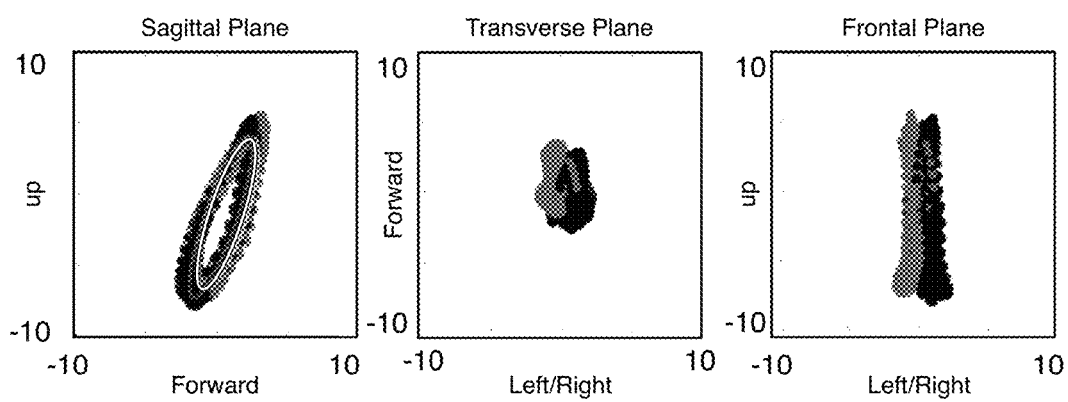
Figure 11C:
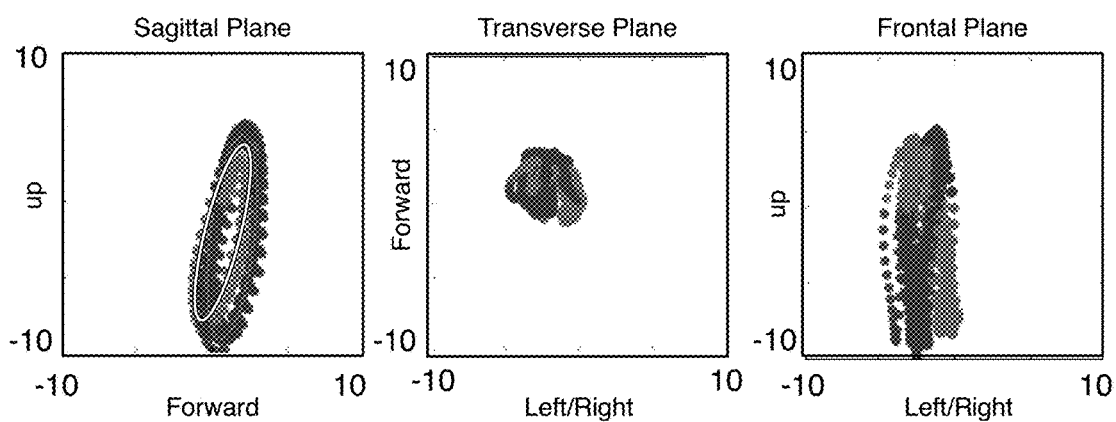

The motion path can be a position over time map for at least one point. Participants will generally have movement patterns that are unique and generally consistent between activities with similar conditions. The position is preferably measured relative to the athlete. The position can be measured in one, two, or three dimensions. As a feature, the motion path can be characterized by different parameters such as consistency, range of motion in various directions, and other suitable properties. In another variation, a motion path can be compared based on its shape. In one implementation, motion paths are analyzed based on a set of motion path heuristics that form a different set of biomechanical signals. Motion path heuristics can be particularly useful in characterizing quality of a participant as well as differentiating smaller style influences. A motion path and motion path heuristics of a bad runner (as shown in FIG. 11A) can be distinctly differentiated from a good runner (as shown in FIGS. 11B and 11C). A bad runner will generally have signs of irregularity in motion shape and more variance. However, even two good runners that conform to the general principals of patterns that make a runner good can be differentiated as shown through a comparison of FIGS. 11B and 11C.

In one approach, motion paths can be compared against an elliptical model (i.e., a set of motion path or "loopiness" heuristics). An ellipse is preferably used as the base shape. Alternative shapes or paths could similarly be used. When running, an activity monitoring device attached to the user in the pelvic region will experiences generally elliptical motion when projected in the sagittal plane. The observed motion path can deviate from this with variations in form and fatigue level.

As shown in FIG. 19, using a set of motion path heuristics include fitting an ellipse to a motion path and analyzing the ellipse to the motion path. Analyzing the ellipse can include measuring a major axis, measuring the minor axis, measuring the angle, measuring the root mean squared error, measuring the x-offset, and the y-offset. Alternative properties such as ellipse length and eccentricity or other properties of a matched ellipse or shape could be used. The root mean squared error can be an indicator of the consistency or "fuzziness" of a motion path. A more consistent motion path will generally have a lower root mean squared error value. The x-offset and y-offset can relate to the amount of variation in the motion path. The set of motion path heuristics may be used on motion path data that is a combination of right and left data. A single plane, such as the sagittal plane, may be analyzed for motion path heuristics, but multiple planes could be analyzed. Alternatively motion path heuristics can be used for the right side and left side independently.

Additionally, the biomechanical signals can include left/right detection, which may be applied for further categorizing or segmenting of biomechanical signals according to the current stride side. For example, left and right steps may result in different motion path patterns. As shown in FIGS. 11A-11C, motion path derived signals can be generated for the right and left steps.

In one preferred implementation, a running signature can include a set of motion path derived signals (e.g., a major axis measurement, a minor axis measurement, ellipse angle, root mean squared error, x-offset, and y-offset), ground contact time, pelvic tilt, pelvic rotation, pelvic drop, cadence, and step impact. Other suitable combinations can be used.

In another variation, a running signature could utilize a kinetic sequence that can be stored and analyzed for running and walking strides or steps. The kinematic data from a step as shown in FIG. 7A may include several kinematic patterns that can be used in characterizing a performance signature. The average velocities and accelerations, local maximums or minimums, relative timing of sequencing events, and other features of the foot and pelvis throughout the stance phase and swing phase of a foot can be used as a signature to identify the user.

For a golfer, a golf swing kinetic sequence signature can include back swing speed, backswing duration, backswing angle, swing path, swing speed, pelvic rotation, follow through path, follow through angle, and other suitable features. As shown in FIG. 7B, a kinetic sequence for golfing can be defined around the detection and timing of rotational speed for the pelvis, thorax, arm, and club. As the golf swing includes a sequence of connected actions (e.g., backswing, the swing, and follow-through), the sequence timing and calculated acceleration and velocities relative to each other of golf swing events can additionally be used as one or more features. As shown in the example of FIG. 7B, a sequence of peak angular velocity at various monitored points can be: pelvis, thorax, arm, and club. The timing between this sequence and the relative or absolute peak angular velocities may additionally be used. The performance features may be used in their original form within the performance signatures, but may alternatively be weighted or processed in any suitable manner when generating the performance signature. Kinetic sequencing of other activities could alternatively be used.

The nature of an action can be influenced by various factors. For example, how a participant performs an action at the start of an activity can be very different from how the participant performs the action after sustained period. Additionally, the objective and/or result of different actions can vary. For example, a golf swing when teeing off will be different from a golf shot when chipping the ball out of a sand pit. Accordingly, the method can include collecting activity condition information of an action. The activity condition information can be associated with the performance signature. The activity condition information can be used in classifying or grouping actions. In some cases, there may be multiple performance signatures associated with different contexts or conditions. For running, activity condition information can include the type of run, the general speed of the run, detected fatigue condition during a run, the ground/environment conditions, and other suitable information. Environment data could include the incline, the type of surface conditions (e.g., paved road, track, dirt path, uneven terrain, etc.), air quality, altitude, and the like. For example, a runner may have a "preferred speed" performance signature that is associated with their running patterns when running within a running speed range, a "sprint" performance signature associated when running above a particular speed, and a "trail-run" performance signature associated with running paths on unpaved or uneven terrain. For golfing, the club type, the distance from the hole, the resulting distance of the hit, the wind or other weather conditions, and/or other activity condition information may be used.

In one variation, the generation of a performance signature is generated for particular conditions. Collected data may only be valid if the environment is within particular threshold. For example, a running signature may only be generated if a run had an elevation change within a certain threshold, the temperature was within a particular range, and the run followed along a road (e.g., did not involve trail running). The method can additionally classify the conditions of an activity so that the performance signature can be dynamically associated with appropriate conditions. An athlete may eventually build up a matrix of performance signals for different conditions. Similarly, the performance signature can be created and associated for particular classification of an activity. For example, a running signature could be for the start, middle, end of a run, or throughout the entire run as a runner fatigues. A golf signature could be for different golf clubs. Alternatively, a performance signature could be a generalized performance signature. For example, a running signature could be an average performance of a whole run. A running signature of a participant could be generated and compared to a performance signature from a similar context such as running on a straight track or treadmill. Alternatively, a performance signature of a participant may be compared to a performance signature generated from a different signature. For example, a runner could have her run compared to a normal Olympian's run even when the run of the participant is a different distance and generated under different conditions. In one exemplary application of activity condition information, the method can include collecting location information during the activity; mapping the location information to a terrain classification; and wherein generating a performance signature comprises generating at least a first signature of a user for a first terrain classification and a second signature of the user for a second terrain classification.

In one variation, the performance signature can characterize a single action, session, or period. For example, a performance signature can be generated for a single run, a single golf swing, or a single swim race. Alternatively, when combining the performance features to form a performance signature, previously collected performance features and/or a previous performance signatures can be factored into the generation of an updated performance signature. In one variation, a performance signature could be the average of signatures from multiple sessions. For example, a running signature could be the average of the runner's current and past running signatures from the last ten runs.

Block S120, which includes collecting performance signatures of the set of participants, functions to obtain a plurality of performance signatures. The performance signatures can be collected with the associated data such as condition information, activity classification, and/or performance metrics. In one variation, a device of the participant transmits the performance signatures to a cloud computing platform. Alternatively, the raw or partially formatted data is collected, and the performance signature can be created in the cloud. A performance is preferably utilized within the context of multiple performance signatures to which a performance signature can be compared. The performance signatures are preferably collected from different participants. Preferably, participants can acquire a sensing device and/or user application to facilitate the generation of a personal performance signature, and then that personal performance signature is synchronized to a remote performance signature storage system. In some implementations, performance signatures of different participants can be processed. In one variation, the set of performance signatures may be indexed so that a performance signature query can be executed to identify a prioritized list of relevant performance signatures. In another variation, a prototypical performance signature, which is a representative performance signature, could be generated from a subset of the performance signatures. A prototypical performance signature can be created for various subgroups and may be used as a target for participants. These may be automatically generated, but could alternatively be manually configured by an administrator. For example, an administrator of the platform could set particular participants to be used in generating a prototypical performance signature to use in comparisons or as a reference.

Figure 9:
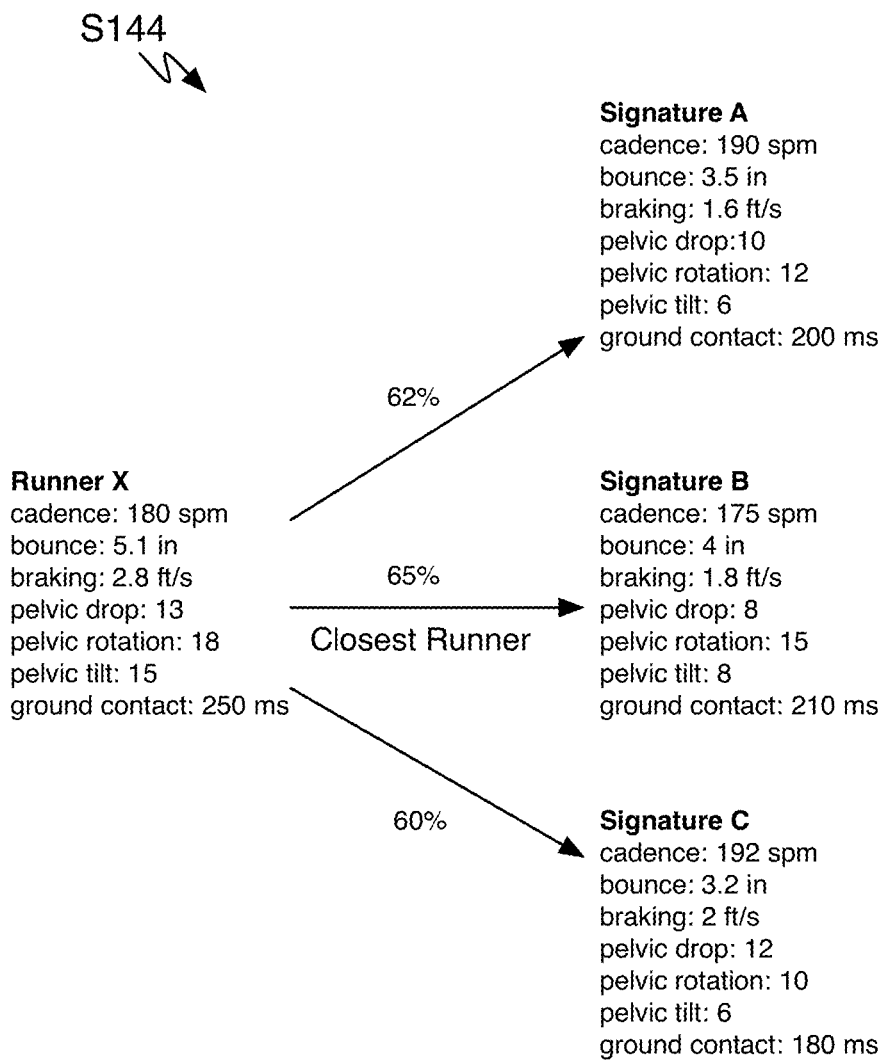
FIG. 9 is an exemplary schematic representation of performance signature comparison and similarity detection.

Block S130, which includes comparing the performance signature of the at least one participant to at least a second performance signature, functions to assess the similarity or differences of at least two performance signatures. The nature of the comparison can depend on the manner in which the comparison will be applied. The comparison of a performance signature may be used in identifying a similar performance signature, in grouping or classifying performance signatures, in characterizing the difference between one or more performance signatures, or sorting performance signatures. As shown in FIG. 9, performance signatures may be compared by performing some comparison heuristic across the set of performance features that make up the performance signature. A performance signature can be compared to a single performance signature. A performance signature may alternatively be compared or used to query a set of performance signatures. The comparison can be executed in a cloud platform where the set of performance signatures have been collected in block S120. Alternatively, the comparison can be executed locally on a sensor device or a user application used by the participant. In some implementations, the method may not utilize an explicit comparison.

Block S140, which includes applying a result of the comparison to an interaction with at least one participant, functions to use a comparison of performance signatures for various applications. A performance signature can be applied in a variety of use-cases.

Figure 8:
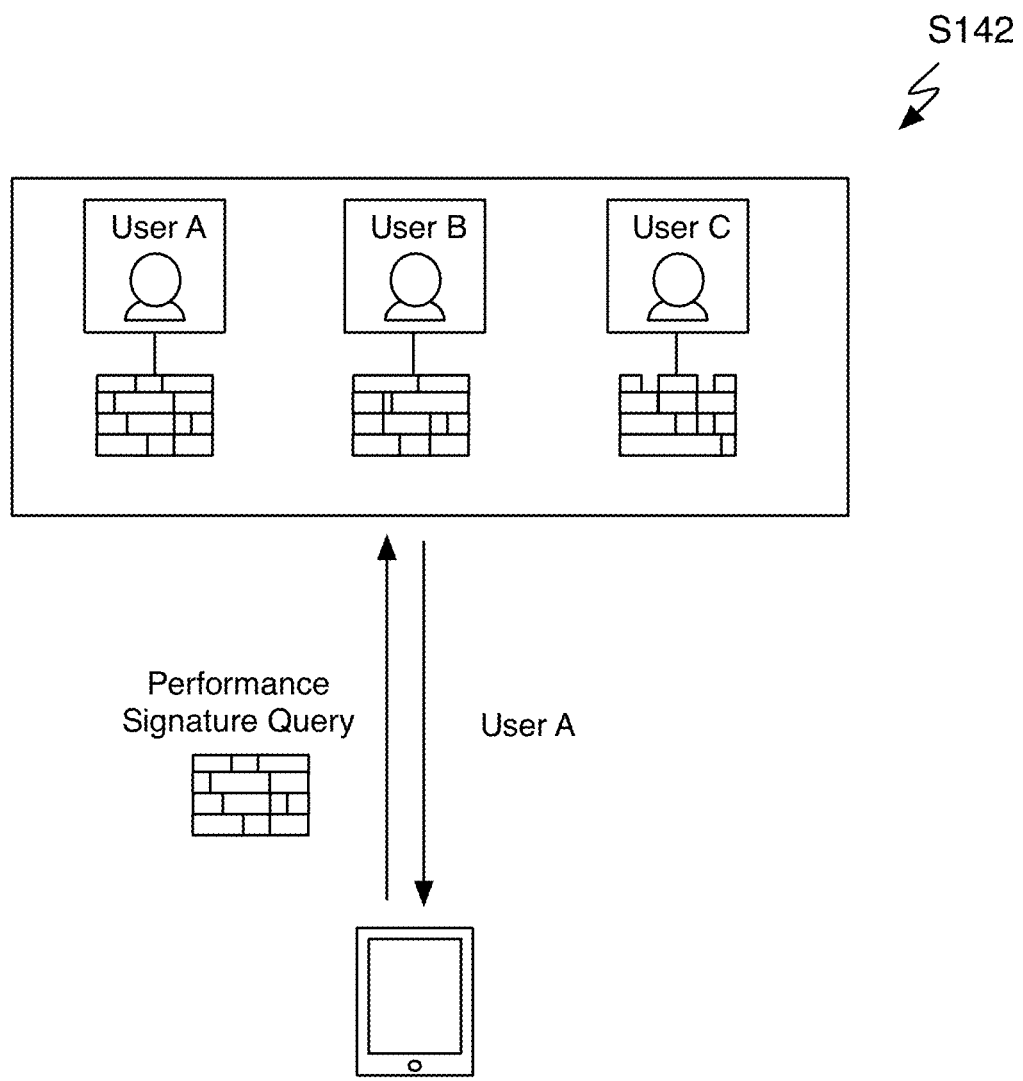
FIG. 8 is a schematic representation of identifying a participant through a performance signature.

In a first use-case, applying a performance signature can include determining a participant identity through a detected performance signature S142. The performance signature can be used to identify an individual. The performance signature could be used in authenticating the user as a form of biometric authentication. Additionally, the performance signature could be used in distinguishing between a small set of participants. Similarly, an identifier (e.g., an account or user profile identifier) can be associated with a performance signature. Comparing the performance signature and applying the comparison can include mapping a user profile to each performance signature of a set of participants, querying performance signatures of the set of participants for at least one matching performance signature similar to the performance signature, and selecting the user profile mapped to the matching performance signature as shown in FIG. 8. Mapping can be a data association using direct or indirect referencing. Querying performance signatures preferably identifies a prioritized list of possible performance signatures that match or are similar to a query performance signature (e.g., the performance signature of the participant). The matching process may generate a probability or score associated with the match. The selection of the user profile may be an automatic selection of the most likely performance signature match. When there is a set of likely matches, the matching result may be used in combination with other user profile selection processes (e.g., user selection of a top possible results) to facilitate selection.

The identifier may be used within a digital online community to characterize their performance style or be used to personalize a selection of relevant coaching services, shoes, apparel, or other running specific services that could help a runner with a specific category of running signature. The identifier could be a graphic, a label, an icon, or any suitable identifier. In one case, the performance signature can serve as one option for a secondary factor of authentication. For example, when signing into a website, a username and password may be used as a primary form of authentication while the walking signature over the last 30 minutes can be used as a default secondary factor of authentication.

The performance signature comparison may be used in identifying participants with a similar style S144. One or more similar runners could be detected to have similar performance signatures. A score could be assigned to the similarity as shown in FIG. 9. For example, participants could find coaches or running groups that have a similar running style. Additionally, relevant products and services such as shoes, apparel, or coaching services can be tailored to each individual based on their running style. This can also pertain to identifying the most relevant products for golfers with a specific swing, and other sports. Performance signatures can be classified by demographics or region, and help explain how different cultures run—i.e. how the Kalenjin tribe in Kenya produces some of the fastest long distance runners in the world, or how runners' performance signatures change as experience/training/gender/aging factors play a role.

Figure 10:
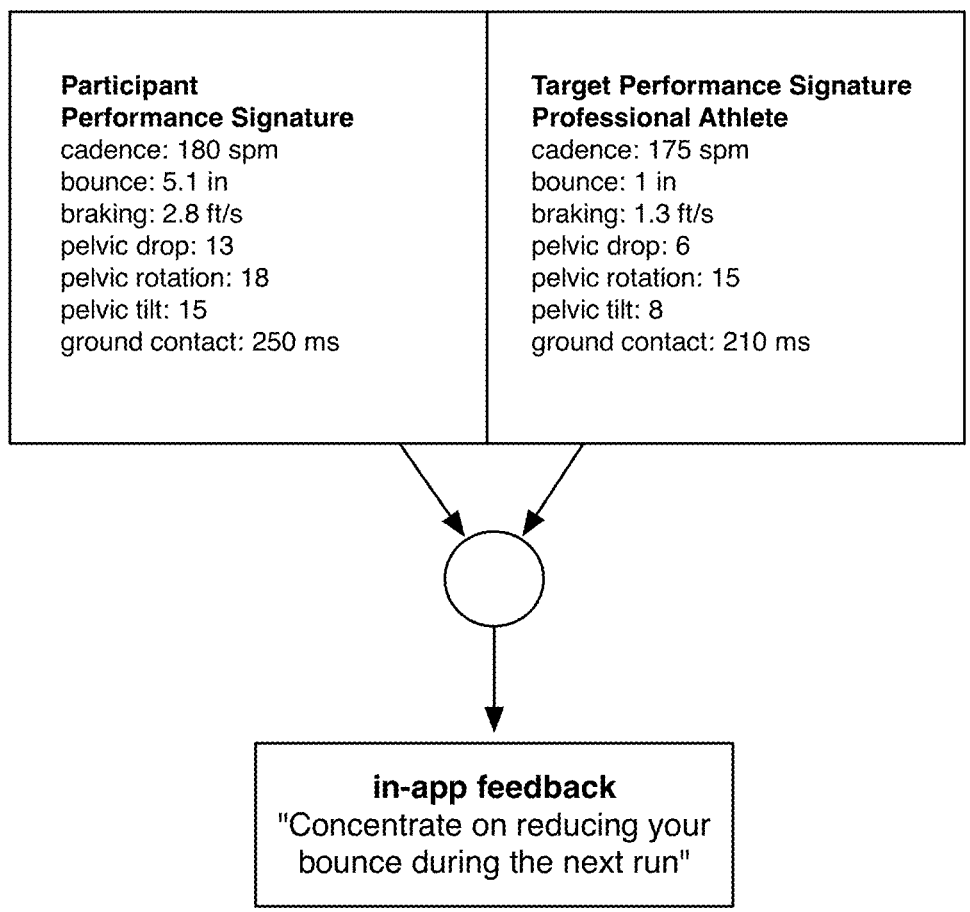
FIG. 10 is a schematic representation of generating a training recommendation based on a second performance signature.
Figure 12:
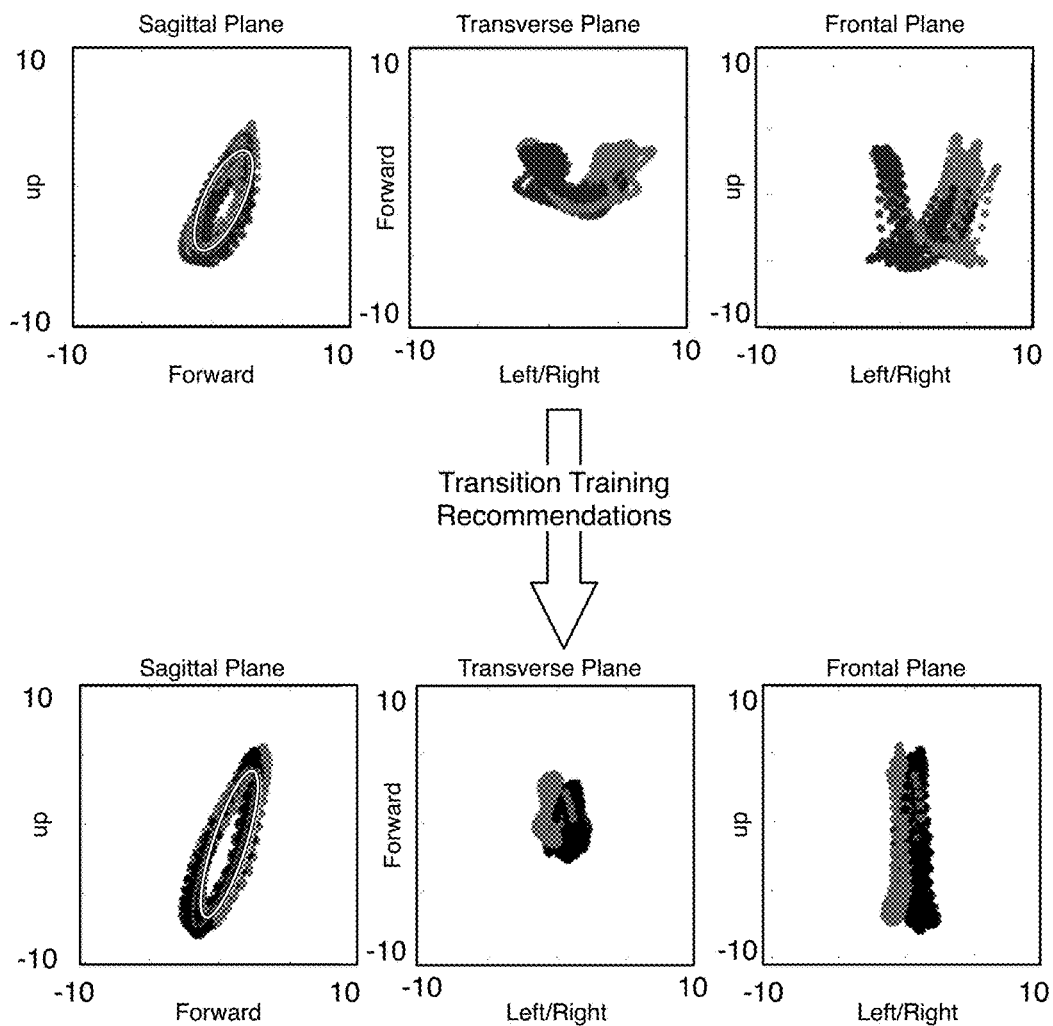
FIG. 12 is an exemplary transformation of a motion path of a runner after following transition training recommendations.

Comparing participants may additionally be used in generating a training recommendation to transition a performance signature towards a second performance signature S146 as shown in FIG. 10, which functions to coach an individual to perform an action more like another athlete or class of athlete. Such training recommendations may help an individual adjust their performance style to approximate a professional athlete or other suitable prototypical athlete. The second performance signature is preferably selected from a set of possible target performance signatures. In one variation, the participant can select a target performance signature. For example, the participant may select a performance signature based on a famous athlete or team. In an alternative embodiment, the second performance signature may be automatically selected. For example, one performance signature may be selected from a five potential target performance signatures based on which most closely matches the current performance signature, which functions to coach an individual based on their current tendencies. In one implementation, the performance signatures of experienced athletes can be collected and used as an aspirational prototypical performance signature for less experienced athletes. Performance signatures of ideal athletes may be averaged or otherwise combined. For example, a single prototypical Olympic marathoner running signature can be formed from ten Olympic runners. Training recommendations, form recommendations, and other forms of feedback can be generated to help a participant run more like an Olympic marathoner or a specific Olympic runner or elite athlete the user admires or has similar biomechanical stride characteristics to. Transitioning training recommendations can provide coaching during an activity or after the activity. A set of different recommendations may be required to fully transition an individual to a new performance signature. In one variation, a single aspect is a focus for each run. Over multiple runs the running style of an individual can change. As shown in one exemplary scenario FIG. 12, a running path and/or other biomechanical properties can see significant changes. This can have benefits if an individual wants to learn how to run in a particular style, run a particular race, or feel more connected to the elite runner. Furthermore, elite runners can be compared to other elite runners in real time during competitive events where commentators, coaches or event observers can engage at a deeper level (beyond pace and overall time) by being able to view & analyze elite runner's instantaneous and aggregated performance signatures in real-time as they compete. For golf, this can enable recreational golfers to compare their swing mechanics to professional golfers. In weight lifting, weight lifters can use performance signatures based on ideal form to target proper form and to avoid form that can put them at a risk for injury. This will help athletes train and compete smarter, and provide new ways for athletes and the larger community to connect on and offline in running, golfing or other sports.

Comparing participants may additionally be used in combination with other performance data in determining how various performance features impact performance results. Used in combination with automated training, the method can be used to determine the best way to train a particular individual that is working towards a particular goal. Additionally, comparisons of performance signatures and how they deteriorate over time or distance throughout a training session or competitive event will help competitors train and compete smarter in running, golfing and other sports. Deterioration of a performance signature can also be used to identify fatigue and alert a user to help avoid injury in running, golfing and other sports.

The systems and methods of the embodiments can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

We claim:

1. A method comprising:
   for a first participant performing an activity, generating a set of performance features during an activity of the first participant;
   wherein at least a subset of the performance features are generated by:
   collecting kinematic data from at least one inertial measurement unit that is attached to a body portion of the first participant, and
   generating a set of biomechanical signals that are, at least in part, based on the kinematic data, wherein the set of biomechanical signals comprises a first plurality of biomechanical signals, wherein each biomechanical signal quantifies at least a portion of a motion executed during the activity of the first participant, wherein the biomechanical signals are ground contact time, braking, pelvic rotation, pelvic tilt, pelvic drop, vertical oscillation of the pelvis, and forward velocity properties of the pelvis;
   combining the set of performance features into a first performance signature;
   comparing the first performance signature to at least a second performance signature of a second participant engaged in the same activity as the first participant, wherein the second performance signature comprises a second plurality of biomechanical signals, wherein each biomechanical signal of the second plurality of biomechanical signals quantifies at least a portion of a motion being executed during the activity of the second participant; and
   providing a training recommendation to the first participant based on the comparing, wherein the training recommendation specifies one or more of the biomechanical signals the first participant is required to change to more approximately emulate the second performance signature of the second participant.

2. The method of claim 1, further comprising:
generating at least a second performance signature from a set of participants;
comparing the first performance signature of the first participant to at least the second performance signature; and
applying a result of the comparison to an interaction with at least one participant.

3. The method of claim 2, further comprising selecting the second performance signature as a target performance signature of the first participant; and wherein applying the result of the comparison comprises generating training recommendations to transition the first performance signature towards the target performance signature according to the comparison.

4. The method of claim 2, wherein applying the result of the comparison to an interaction with at least one participant comprises authenticating a user account of the at least one participant.

5. The method of claim 1, wherein the kinematic data is collected from a first inertial measurement unit positioned at a first location and a second inertial measurement unit positioned at a second location.

6. The method of claim 1, wherein the performance signature is for a repetitive action; and wherein generating a set of biomechanical signals comprises segmenting the kinematic data into a consecutive sequence of actions.

7. The method of claim 6, wherein the performance signature is generated for sequences of actions when a participant pace metric is within a pace range.

8. The method of claim 6, wherein the activity is running and wherein segmenting the kinematic data into a consecutive sequence of actions comprises segmenting the kinematic data into a consecutive sequence of running steps.

9. The method of claim 8, further comprising collecting location information during the activity; mapping the location information to a terrain classification; and wherein generating a performance signature comprises generating at least a first signature of the participant for a first terrain classification and a second signature of the participant for a second terrain classification.

10. The method of claim 6, wherein the activity is swimming and wherein segmenting the kinematic data into a consecutive sequence of actions comprises segmenting the kinematic data into a consecutive sequence of swimming strokes.

11. The method of claim 6, wherein the activity is biking and wherein segmenting the kinematic data into a consecutive sequence of actions comprises segmenting the kinematic data into a consecutive sequence of pedal strokes.

12. The method of claim 1, wherein the performance signature is an isolated action; and wherein generating a set of biomechanical signals comprises selecting a window of kinematic data associated with an action.

13. The method of claim 12, wherein the activity is golfing and wherein the window of kinematic data is associated with a golf swing.

14. The method of 12, wherein the activity is weight lifting and wherein the window of kinematic data is associated with a weight lifting action.

15. A system comprising:
at least one activity monitor device coupled to a location affected by the action of the participant, wherein the at least one activity monitor device is mounted to clothing worn by the participant; and
a processor communicatively coupled to the at least one activity monitor, wherein the processor is configured to:
  isolate kinematic data associated with an action of an activity;
  generate a set of biomechanical signals based on the isolated kinematic data wherein the biomechanical signals are ground contact time, braking, pelvic rotation, pelvic tilt, pelvic drop, vertical oscillation of the pelvis, and forward velocity properties of the pelvis;
  assemble a set of performance features, of which at least a subset of the performance features are based on the set of biomechanical signals;
  generate a performance signature with the set of performance features;
  determine at least one difference between the performance signature and a target signature; and
  inform the participant of the at least one difference to assist the participant in modifying performance of the activity to better emulate the target signature, wherein the at least one difference includes one or more of the biomechanical signals.

16. The system of claim 15, further comprising:
a computing platform configured to:
  collect multiple performance signatures from a plurality of participants,
  receive performance signature queries, and
  generate a comparison between a performance signature query and at least a second performance signature.

17. The system of claim 15, wherein the performance signature is for a repetitive action; and wherein the processor is configured to segment the kinematic data into a consecutive sequence of actions when generating a set of biomechanical signals.

18. The method of claim 17, wherein the activity is running and wherein the processor configured to segment the kinematic data into a consecutive sequence of actions is further configured to segment the kinematic data into a consecutive sequence of running steps.

19. The method of claim 15, wherein the performance signature is an isolated action; and wherein the processor is configured to select a window of kinematic data associated with an action when generating a set of biomechanical signals.

20. The system of 19, wherein the activity is golfing and wherein the window of kinematic data is associated with a golf swing.

* * * * *